(12) United States Patent
McNeer

(10) Patent No.: US 12,140,463 B1
(45) Date of Patent: Nov. 12, 2024

(54) METHOD INCLUDING OPTICAL DETECTION

(71) Applicant: PointSiana Solutions, LLC, Miami, FL (US)

(72) Inventor: Richard McNeer, Miami, FL (US)

(73) Assignee: PointSiana Solutions, LLC, Miami, FL (US)

( * ) Notice: Subject to any disclaimer, the term of this patent is extended or adjusted under 35 U.S.C. 154(b) by 0 days.

(21) Appl. No.: 18/542,264

(22) Filed: Dec. 15, 2023

Related U.S. Application Data

(60) Provisional application No. 63/581,151, filed on Sep. 7, 2023.

(51) Int. Cl.
*G01F 22/00* (2006.01)
*A61M 5/142* (2006.01)
(Continued)

(52) U.S. Cl.
CPC ......... *G01F 22/00* (2013.01); *A61M 5/14276* (2013.01); *A61M 5/1684* (2013.01);
(Continued)

(58) Field of Classification Search
None
See application file for complete search history.

(56) References Cited

U.S. PATENT DOCUMENTS 7,654,982 B2 * 2/2010 Carlisle ............... A61M 5/1483
604/132
8,315,684 B2 * 11/2012 Petersen ............... A61B 5/7228
600/336

(Continued)

FOREIGN PATENT DOCUMENTS

EP 0622615 B1 12/1997

OTHER PUBLICATIONS

Monk, Arduino Lesson 9. Sensing Light, Adafruit Industries, retrieved from: https://learn.adafruit.com/adafruit-arduino-lesson-9-light, material updated: Aug. 29, 2023, 12 pages.
(Continued)

*Primary Examiner* — Brandi N Hopkins
*Assistant Examiner* — Nigel H Plumb
(74) *Attorney, Agent, or Firm* — HOLLOWELL PATENT GROUP; Kelly Hollowell

(57) ABSTRACT

Apparatus and associated methods disclosed herein relate to configuring a light emitter to direct emitted light having a preselected wavelength through a liquid retained by a collapsible reservoir to a light sensor disposed in the collapsible reservoir, determining a distance separating the light emitter from the light sensor across the collapsible reservoir interior based on the amount of emitted light absorbed by the liquid, and determining the volume of the liquid retained by the collapsible reservoir based on the distance. The liquid may comprise an active compound formulation. An excipient may be added to the liquid in an excipient concentration governing a linear relationship between distance and light absorption at the preselected wavelength. The distance may be determined as a function of the linear relationship. The risks of abrupt therapy cessation or premature refill may be advantageously reduced by providing real-time remaining liquid volume measurements as the collapsible reservoir collapses.

30 Claims, 12 Drawing Sheets

(51) Int. Cl.
 *A61M 5/168* (2006.01)
 *G01F 17/00* (2006.01)
(52) U.S. Cl.
 CPC .............. *A61M 2202/0007* (2013.01); *A61M 2205/3313* (2013.01); *A61M 2205/50* (2013.01); *G01F 17/00* (2013.01)

(56) References Cited

U.S. PATENT DOCUMENTS

| | | | |
|---|---|---|---|
| 9,255,830 B2* | 2/2016 | Whalley | A61M 5/1689 |
| 10,245,378 B2* | 4/2019 | Raman | A61M 5/14276 |
| 11,458,250 B2* | 10/2022 | Phillips | A61M 5/14593 |
| 2019/0358387 A1* | 11/2019 | Elbadry | A61M 1/361 |
| 2022/0096738 A1* | 3/2022 | Peterson | G01F 17/00 |

OTHER PUBLICATIONS

Rembor, Adafruit LTR-329 and LTR-303 Light Sensors, Adafruit Industries, retrieved from: https://learn.adafruit.com/adafruit-ltr-329-ltr-303, material updated: Aug. 29, 2023, 21 pages.

Lady Ada, Adafruit TSL2591 High Dynamic Range Digital Light Sensor, retrieved from: https://learn.adafruit.com/adafruit-tsl2591, material updated: Aug. 29, 2023, 26 pages.

Davis, An Introduction to Laser Diodes, Technical Article, retrieved from: https://www.allaboutcircuits.com/technical-articles/an-introduction-to-laser-diodes/, Jun. 12, 2017, 10 pages.

Donnelly, Introduction to the Spectrophotometer: Wavelength, Absorbance, and Concentration in Methylene Blue, Sample Lab Report, Mar. 2, 2006, 8 pages.

Arduino—Control LED Brightness with a Potentiometer—The Robotics Back End, Arduino Tutorial, retrieved from: https://roboticsbackend.com/arduino-control-led-brightness-with-a-potentiometer/; retrieved on Nov. 2, 2023, 8 pages.

Arduino LED—Complete Tutorial, retrieved from: https://roboticsbackend.com/arduino-led-complete-tutorial/; retrieved on Nov. 2, 2023, 18 pages.

Arduino Potentiometer—Complete Tutorial, retrieved from: https://roboticsbackend.com/arduino-potentiometer-complete-tutorial/; retrieved on Nov. 2, 2023, 9 pages.

Arduino Potentiometer with Multiple LEDs [Tutorial], retrieved from: https://roboticsbackend.com/arduino-potentiometer-with-multiple-leds-tutorial/; retrieved on Nov. 2, 2023, 14 pages.

Beer-Lambert Law, retrieved from: https://en.wikipedia.org/w/index.php?title=Beer-Lambert_law&oldid= 1181360014; Oct. 22, 2023; 12 pages.

8:2 Beer's Law, Chemistry Libre Texts; retrieved from: https://chem.libretexts.org/Courses/Providence_College/CHM_331_Advanced_Analytical_Chemistry_1_/08%3A_An_I ntroduction_to_ Ultraviolet-Visible . . . ; retrieved on Nov. 5, 2023; 4 pages.

Reese, Color Balancing Video Camera Light Feat. DotStars, https://learn.adafruit.com/color-balancin-light-box-with-dotstar-cool-warm-white-leds, material updated: Aug. 29, 2023, 40 pages.

Singh et al., Comparative Evaluation of Accuracy of Pulse Oximeters and Factors Affecting Their Performance in a Tertiary Intensive Care Unit, J. Clin. Diagn. Res., Jun. 1, 2017, 11(6):OC05-OC08, 10 pages; retrieved from: https://www.ncbi.nlm.nih.gov/pmc/articles/PMC5535407/.

How to Use Beer Lambert Law?, The Institute of Beer, retrieved from: https://theinstituteofbeer.com/beer/how-to-use-beer-lambert-law.html; retrieved on: Nov. 5, 2023, 6 pages.

Chen, How to Apply Additional PWM Intensity Control to LED Drivers, Maxim Integrated, Application Note 4472, Jul. 2, 2010; 6 pages.

Illuminance, retrieved from: https://en.wikipedia.org/w/index.php?title=illuminance&oldid=1180514051; Oct. 17, 2023; 5 pages.

Singh et al., Comparative Evaluation of Accuracy of Pulse Oximeters and Factors Affecting Their Performance in a Tertiary Intensive Care Unit, Journal of Clinical Diagnostic Research, Jun. 2017 vol. 11(6):OC05-OC08, 4 pages.

Laser Diode, retrieved from: https://en.wikipedia.org/w/index.php?title=laser_diode&oldid=1176876905; Sep. 24, 2023; 16 pages.

Margaret, Laser vs. LED: Difference between LED and Laser Light Source, FS Community, retrieved from: https://community.fs.com/article/difference-between-laser-light-source-and-led-light-source.html; updated: Sep. 29, 2021; 2 pages.

Morgan, Light Sensors: Units, Uses, and How They Work, Sensors & Data Acquisition, Environmental Sensors, EndaqBlog; retrieved from: https://blog.endaq.com/how-light-sensors-work; retrieved on: Nov. 2, 2023; 14 pages.

Lumen (unit), retrieved from: https://en.wikipedia.org/w/index.php?title=lumen&oldid=1150479204; Apr. 18, 2023; 6 pages.

Lux, retrieved from: https://en.wikipedia.org/w/index.php?title=lux&oldid=1178187595; Oct. 2, 2023; 9 pages.

Clark, MIDI Laser Harp with Time of Flight Distance Sensors, Adafruit Industries, retrieved from: https://learn.adafruit.com/midi-laser-harp-time-of-flight-senseor, material updated: Aug. 29, 2023, 55 pages.

Photodiode, retrieved from: https://en.wikipedia.org/w/index.php?title=Photodiode&oldid=1150479204; Sep. 11, 2023; 10 pages.

Bryant, Photodiodes and other Light Sensors, Analog Devices Wiki; retrieved from: https://wiki.analog.com/university/courses/electronics/text/light-sensors-photodiodes#phtodiodes_phototransistors; retrieved on: Oct. 23, 2023, 20 pages.

Photoresistor, retrieved from: https://en.wikipedia.org/w/index.php?title=Photoresistor&oldid=1150479204; Apr. 5, 2023; 3 pages.

Photoresistor; Ch. 3—Resistor Types, retrieved from: https://eepower.com/resistor-guide/resistor-types/photo-resistor#, retrieved on: Oct. 23, 2023; 6 pages.

Ralston, et al., Potential errors in pulse oximetry, Anaesthesia, 1991, vol. 46, pp. 291-295.

Yartsev, Principles of pulse oximetry, Deranged Physiology, retrieved from: https://https://derangedphysiology.com/main/cicm-primary-exam/required-reading/respiratory-system/Chapter 410/principles-pulse-oximetry, retrieved on: Oct. 22, 2023, 17 pages.

Astels, Proximity Based Lighting, Adafruit Industries, retrieved from: https://learn.adafruit.com/proximity-based-lighting, material updated: Aug. 29, 2023, 22 pages.

Rubell, PyPortal Philips Hue Lighting Controller, Adafruit Industries, retrieved from: https://learn.adafruit.com/pyportal-philips-hue-lighting-controller, material updated: Aug. 29, 2023, 37 pages.

Prakash, Precision Brightness and colo Mixing in LED Lighting Using Discrete Current Sense Amplifiers, Texas Instruments, TI Tech Notes, SBOA189—Feb. 2017, 3 pages.

TPS92623-Q1EVM User's Guide, Texas Instruments, SLUUCK5—Nov. 2021, 8 pages.

AN-1656 Design Challenges of Switching LED Drivers, Texas Instruments, Application Report, SNVA253A—Oct. 2007, Revised May 2013, 7 pages.

Eichhorn, Analog PWM Dimming in White-LED Drives, Texas Instruments, Application Report, SNVA768—Dec. 2016.

Ng, Using PWM for Dimmer Function in LED Lighting, Texas Instruments, Design Note DN115, SWRU227, Jun. 2009, 9 pages.

TPS92623-Q1 Three-Channel, Automotive High Side LED Driver with Thermal Sharing Control, Texas Instruments, SLVSFS4A—Dec. 2021, Revised Jun. 2022, 38 pages.

Lady Ada, Adafruit TSL2561 Luminosity Sensor, retrieved from: https://learn.adafruit.com/tsl2561, material updated: Nov. 21, 2017, 17 pages.

Administrator, What is a Laser Diode? Its Working, Construction, Different Types and Uses, Electronics Hub, retrieved from: https://www.electronicshub.org/electronic-tutorials, Jan. 20, 2018, 11 pages.

Pudue University, Introduction to Light Emitting Diodes (LEDS); retrieved from: https://engineering.purdue.edu/~ece495/Power_Electronics_Lab/LED_Basics.pdf; retrieved on: Nov. 2, 2023; 6 pages.

* cited by examiner

METHOD INCLUDING OPTICAL DETECTION

CROSS-REFERENCE TO RELATED APPLICATIONS

This application claims the benefit of U.S. Provisional Patent Application No. 63/581,145, titled "Photometric Method to Assess Real-time Volume of an Implanted Reservoir," filed Sep. 7, 2023, by Richard McNeer and the entire content of the above-referenced application is incorporated herein by reference.

TECHNICAL FIELD

The present disclosure relates generally to reservoir volume assessment.

BACKGROUND

Therapeutic fluids are used to treat patients suffering from a variety of medical conditions. For example, a doctor may treat a patient with a therapeutic fluid to alleviate pain, fight infection or kill cancer cells. A therapeutic fluid may be, for example, an anesthetic, an antibiotic, or a chemotherapy drug. The doctor may prescribe a particular therapeutic fluid delivery rate specific to a patient's medical condition. Some therapeutic fluids may be delivered to the patient intravenously from a fluid reservoir or bag. An exemplary intrathecal pump device may deliver therapeutic fluid by injection to the intrathecal space of the patient's spinal cord.

An intrathecal pump device may be surgically implanted in a patient. An intrathecal pump device implant may have a reservoir retaining therapeutic fluid. The reservoir may be a collapsible reservoir. An implanted intrathecal pump device may administer therapeutic fluid from the collapsible reservoir through a catheter inserted in the intrathecal space surrounding the spinal cord. An implanted intrathecal pump device needs to be surgically replaced periodically or refilled when the reservoir is depleted. The implanted intrathecal pump device may need to be replaced or refilled before depletion to avoid abrupt cessation of therapy.

Accurately determining when the therapeutic fluid volume remaining in the collapsible reservoir drops below a predetermined threshold volume may be challenging. For example, a predictive assessment strategy based on variably set pump flow rate and time may be inaccurate at least because actual flow rate is not precise. An estimate of remaining therapeutic fluid volume determined based on flow rate and time may be significantly different from actual volume, especially toward the end of a volume cycle. Inaccurate volume estimates may expose patients to abrupt cessation of therapy when the actual volume is less than estimated. The morbidity added to these patients can be clinically very significant. If the estimated remaining therapeutic fluid volume is less than the actual remaining therapeutic fluid volume, patients may undergo premature pump refill or replacements and associated surgical risks.

SUMMARY

Apparatus and associated methods disclosed herein relate to configuring a light emitter to direct emitted light having a preselected wavelength through a liquid retained by a collapsible reservoir to a light sensor disposed in the collapsible reservoir, determining a distance separating the light emitter from the light sensor across the collapsible reservoir interior based on the amount of emitted light absorbed by the liquid, and determining the volume of the liquid retained by the collapsible reservoir based on the distance. The liquid may comprise an active compound formulation. An excipient may be added to the liquid in an excipient concentration governing a linear relationship between distance and light absorption at the preselected wavelength. The distance may be determined as a function of the linear relationship. The risks of abrupt therapy cessation or premature refill may be advantageously reduced by providing real-time remaining liquid volume measurements as the collapsible reservoir collapses.

9, based on cycling activation of at least two light emitters through at least two respective on and off time periods.

Figure 12:
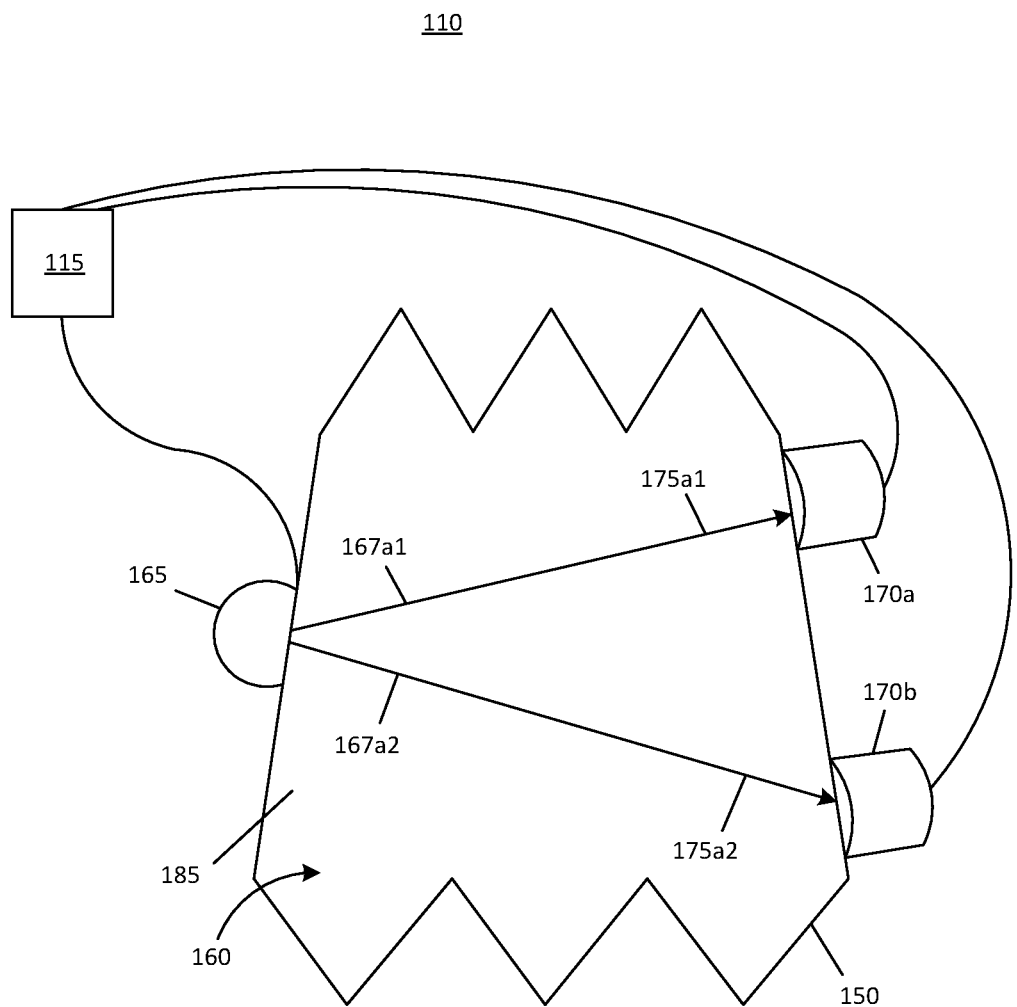

FIG. 12 depicts an exemplary volume assessment implementation configured to determine a distance across a collapsible reservoir interior using one light emitter and at least two light sensors.

Figure 13:
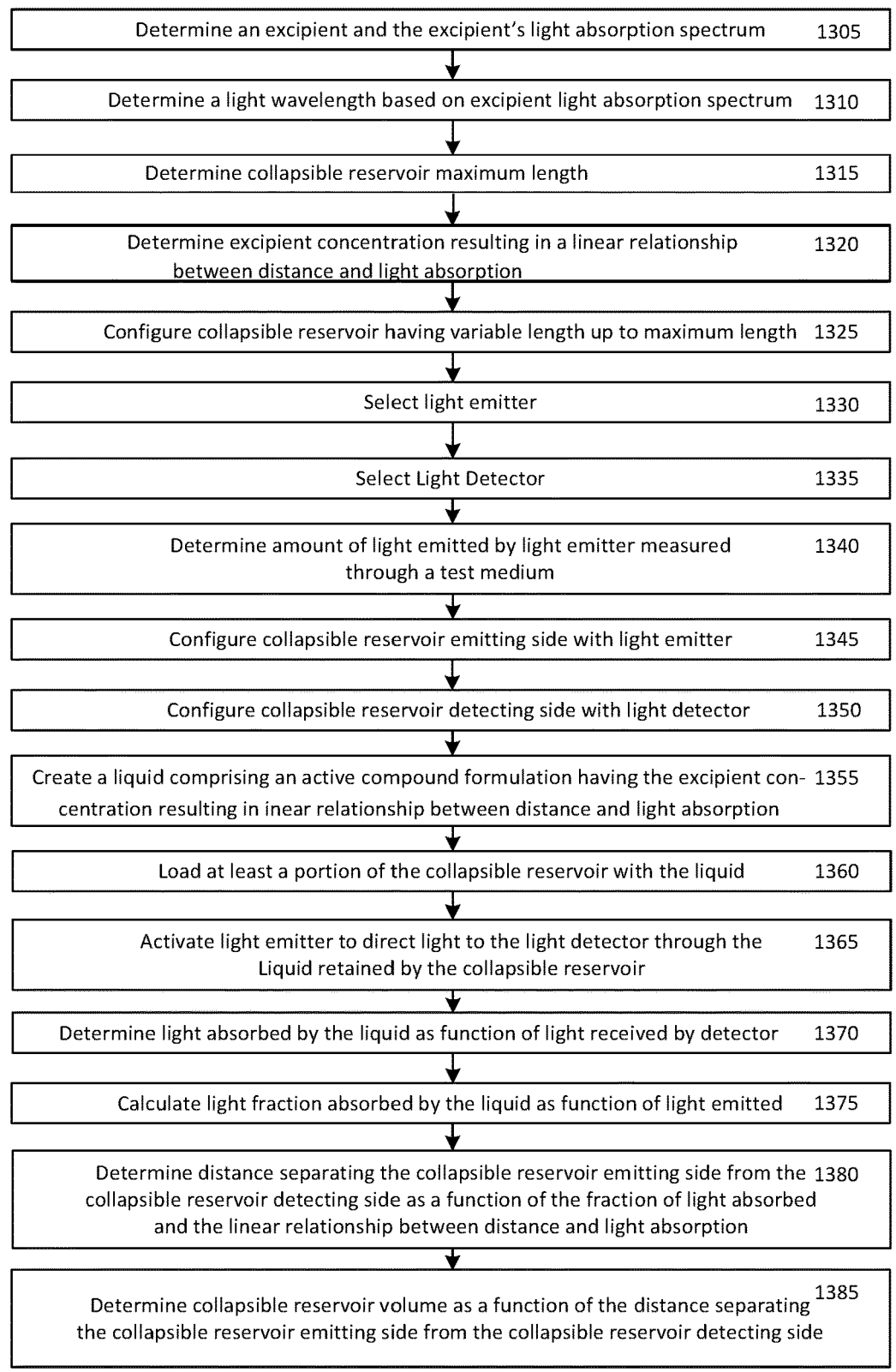

FIG. 13 depicts an exemplary method to make a volume assessment device.

Figure 14:
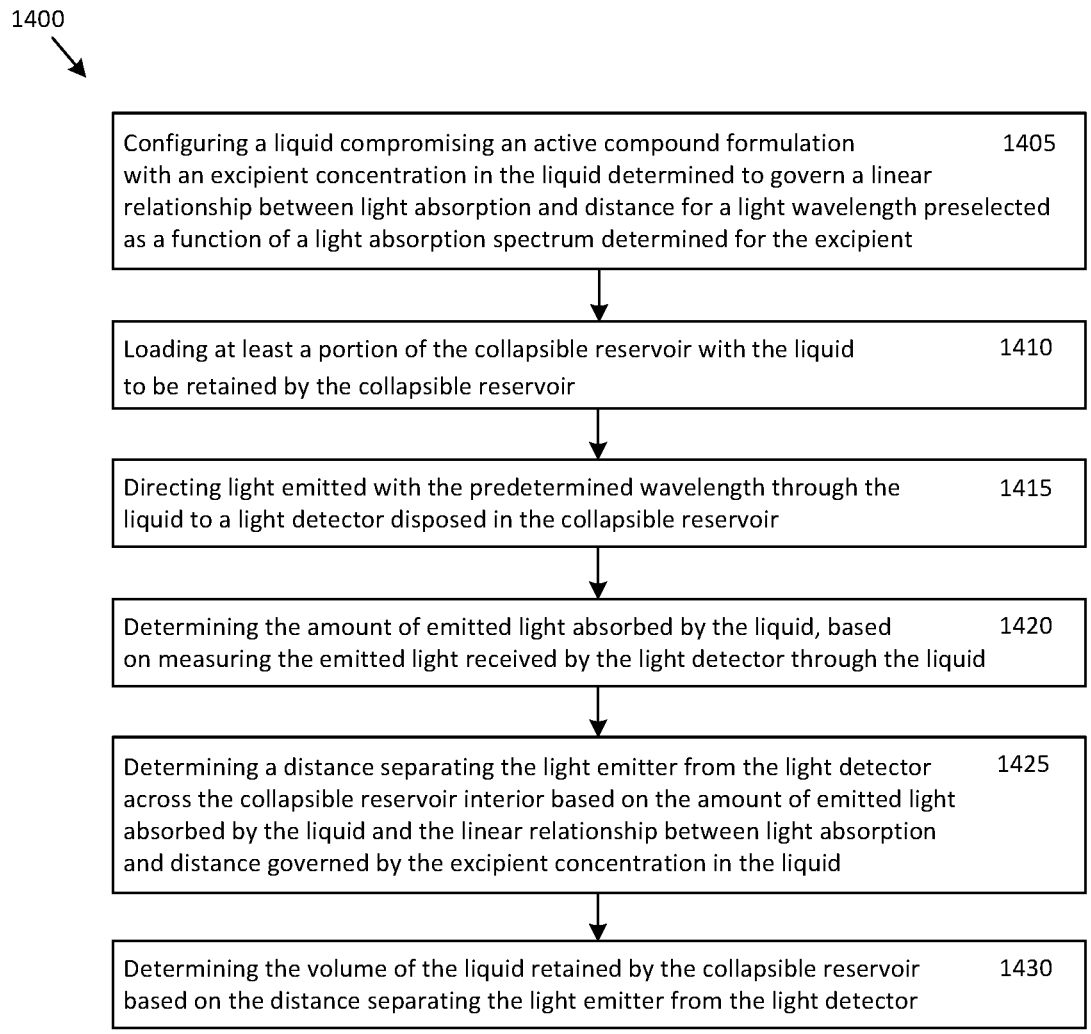

FIG. 14 depicts a process flow of an exemplary volume assessment process.

DETAILED DESCRIPTION OF EXEMPLARY IMPLEMENTATIONS

The detailed description explains exemplary implementations of the present disclosure, together with technical effects and features, by way of examples with reference to the drawings. The flow diagrams and structural block diagrams depicted herein are just examples. There may be many variations to the disclosed processes, apparatuses, components, techniques, or operations described herein without departing from the spirit of the invention. For instance, the steps may be performed in a differing order and steps or components may be added, deleted, or modified. All these variations should be considered as within the scope of the claimed invention. Like reference symbols in the various drawings indicate like elements.

Figure 1:
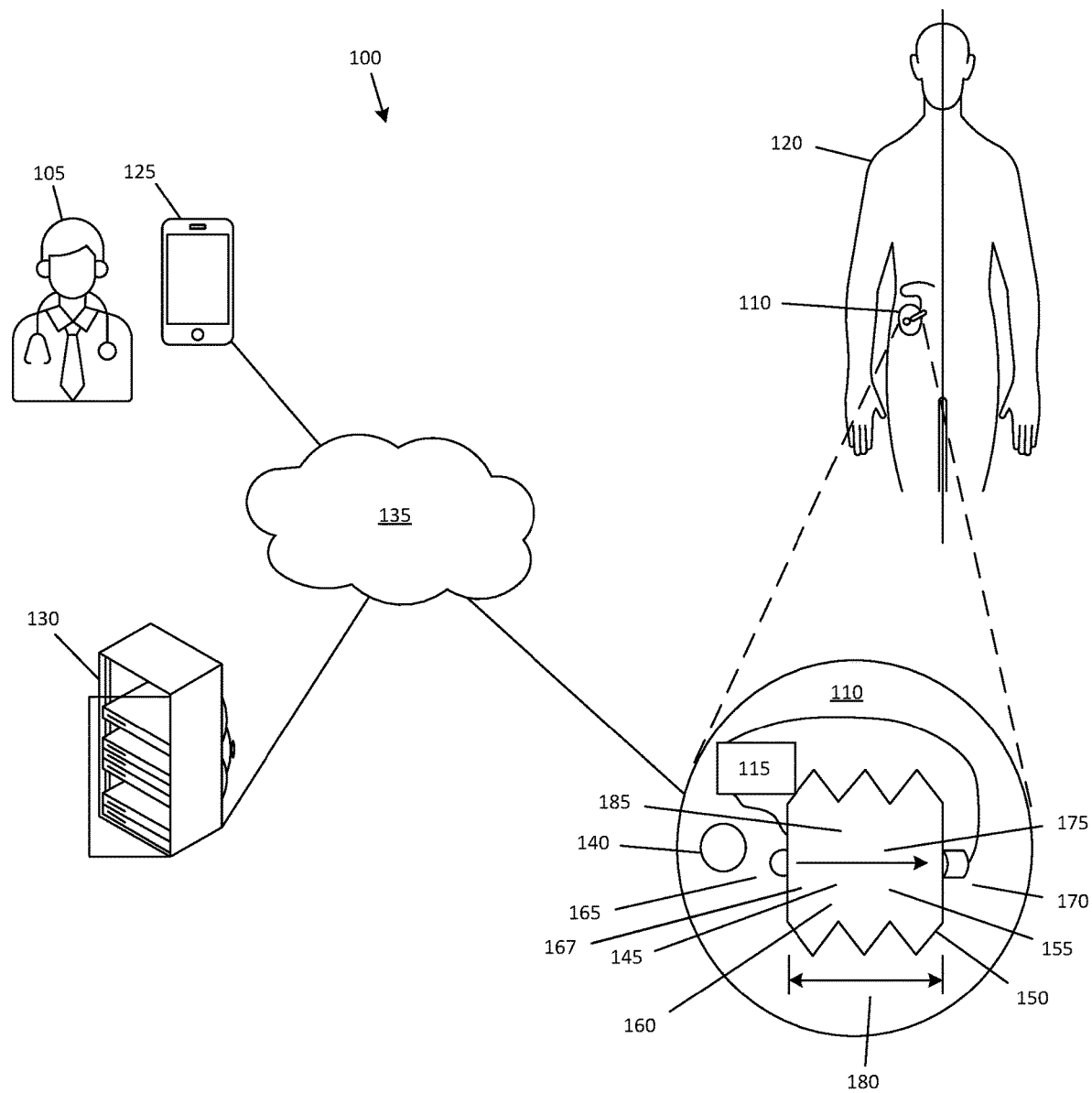
FIG. 1 depicts a volume assessment implementation in an exemplary scenario determining a distance separating a light emitter from a light sensor across a collapsible reservoir interior, wherein the distance is determined based on the amount of emitted light absorbed by a liquid retained by the collapsible reservoir, wherein the liquid comprises an active compound formulation and an excipient, and wherein the excipient is present in an excipient concentration governing a linear relationship between distance and light absorption at a preselected wavelength.

FIG. 1 depicts a volume assessment implementation in an exemplary scenario determining a distance separating a light emitter from a light sensor across a collapsible reservoir interior, wherein the distance is determined based on the amount of emitted light absorbed by a liquid retained by the collapsible reservoir, wherein the liquid comprises an active compound formulation and an excipient, and wherein the excipient is present in an excipient concentration governing a linear relationship between distance and light absorption at a preselected wavelength. In the exemplary volume assessment scenario 100 depicted by FIG. 1, doctor 105 uses the exemplary intrathecal pump device 110 configured with the exemplary volumetric assessment engine (VAE) 115 to treat the patient 120 with a therapeutic fluid. The intrathecal pump device 110 is implanted in patient 120. The intrathecal pump device 110 has an electronic module configured with processor-executable program instructions designed to implement the VAE 115. Doctor 105 uses the mobile device 125 to configure and control the intrathecal pump device 110. In the depicted implementation the VAE 115 is operably coupled with the mobile device 125 and the server 130 via the network cloud 135. Pump 140 delivers therapeutic fluid to the patient 120. Therapeutic fluid comprising the active compound formulation 145 is retained by reservoir 150. The active compound formulation 145 may be, for example, an anesthetic, an antibiotic, or a chemotherapy drug. In the depicted implementation reservoir 150 is a collapsible reservoir. As the therapeutic fluid within the reservoir is depleted the collapsible reservoir 150 collapses. In the depicted implementation excipient 155 has been added to the therapeutic fluid. In the depicted implementation the excipient 155 comprises a dye which absorbs at a selected wavelength of light. In the depicted implementation excipient 155 is present in the therapeutic fluid in the excipient concentration 160. In the depicted implementation excipient concentration 160 is selected so that the relationship between distance through the therapeutic fluid and light absorption at a preselected wavelength is linear. In the depicted implementation the light emitter 165 directs emitted light 167 having the preselected wavelength from one side of the collapsible reservoir 150 through the therapeutic fluid to the light sensor 170 at another side of the collapsible reservoir 150. In the depicted implementation the light sensor 170 quantifies the amount of emitted light 167 received by the light sensor 170. In the depicted implementation the amount of emitted light 167 received by the light sensor 170 is reduced by light absorption 175 through the therapeutic fluid retained by the collapsible reservoir. VAE 115 determines the amount of emitted light 167 absorbed by the therapeutic fluid, as a function of the amount of emitted light 167 received by the light sensor 170 and the amount of emitted light 167 emitted by the light emitter 165. The VAE 115 calculates the distance 180 the emitted light 167 must travel through the liquid 185 mixture comprising therapeutic fluid and excipient 155 before reaching the light sensor 170. The VAE 115 calculates the distance 180 determined as a function of the amount of emitted light 167 absorbed by the therapeutic fluid. The distance 180 varies as a function of the collapsible reservoir 150 volume. VAE 115 determines the volume of the collapsible reservoir 150 calculated as a function of the distance 180. In the depicted implementation the VAE 115 is configured to send real-time measurements of therapeutic fluid volume remaining in the intrathecal pump device 110 to the server 130 via the network cloud 135, as the therapeutic fluid is depleted and the collapsible reservoir 150 collapses.

Figure 2:
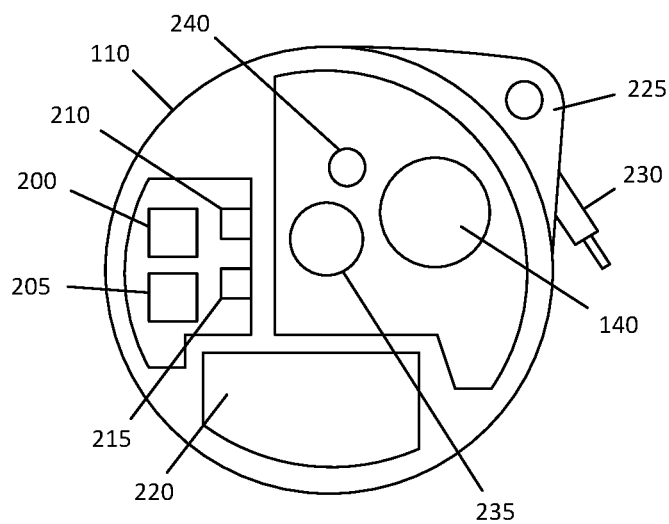
FIG. 2 depicts a top plan view of an exemplary intrathecal pump device.

FIG. 2 depicts a top plan view of an exemplary intrathecal pump device. In FIG. 2, the exemplary intrathecal pump device 110 includes an electronic module comprising the computer processor 200 and the computer memory 205. In the depicted implementation the intrathecal pump device 110 electronic module includes the input/output (I/O) interface 210 and the communication interface 215. The computer processor 200, the computer memory 205, I/O interface 210 and the communication interface 215 are described further with reference to FIG. 4 herein. In the depicted implementation the intrathecal pump device 110 includes the battery 220 configured to electrically power the intrathecal pump device 110 electronic module and the pump 140. The battery 220 may be a rechargeable battery. In the depicted implementation the pump 140 is a peristaltic pump. In the depicted implementation the side catheter access port 225 permits maintenance or adjustment of a catheter in fluid communication with the catheter port 230. In an illustrative example, the intrathecal pump device 110 may deliver therapeutic fluid retained by the collapsible reservoir 150 (depicted for example at least by FIGS. 1, 3, and 7-12) through the catheter. The therapeutic fluid may comprise medication to be administered via the catheter to a patient's intrathecal space. In the depicted implementation the intrathecal pump device 110 includes the reservoir port 235 configured to permit refilling the collapsible reservoir 150. In the depicted implementation the intrathecal pump device 110 includes the antenna 240. The antenna 240 may be an antenna configured to permit wireless data communication between the intrathecal pump device 110 and an external computer-implemented system. The antenna 240 may be configured in the communication interface 215.

Figure 3:
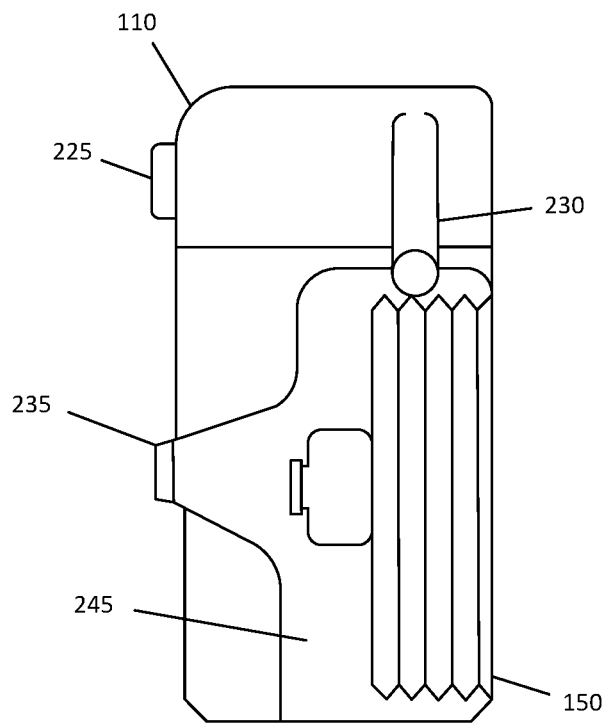
FIG. 3 depicts a side view of the exemplary intrathecal pump device depicted by FIG. 2.

FIG. 3 depicts a side view of the exemplary intrathecal pump device depicted by FIG. 2. In the implementation depicted by FIG. 3, the collapsible reservoir 150 is retained within the cavity 245. The cavity 245 may be pressurized. The cavity 245 may be pressurized to a cavity interior pressure greater than collapsible reservoir 150 interior pressure.

Figure 4:
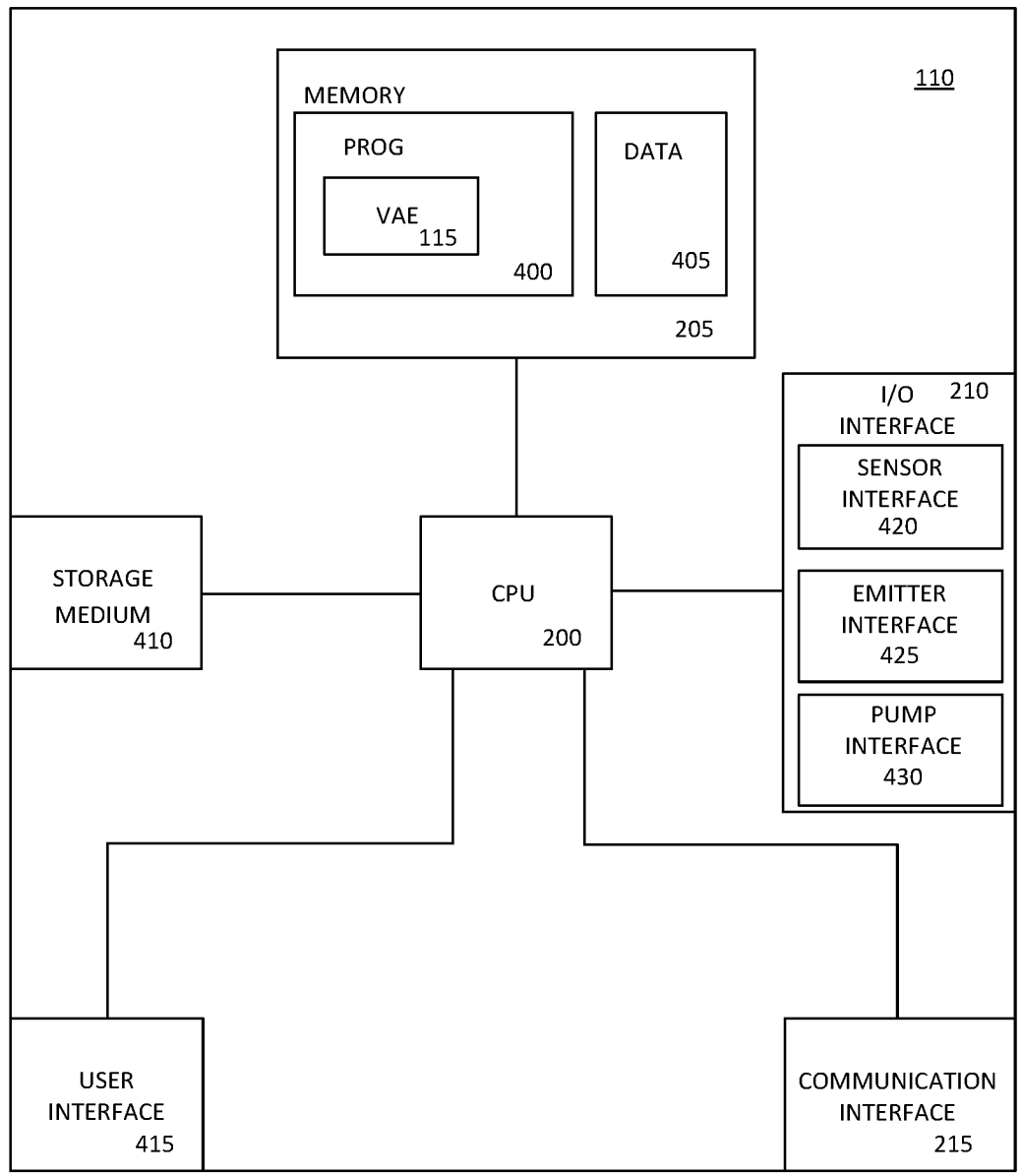
FIG. 4 depicts a schematic view of an exemplary intrathecal pump device electronic module configured with a volumetric assessment engine (VAE) designed to determine a distance separating a light emitter from a light sensor across a collapsible reservoir interior, wherein the distance is determined based on the amount of emitted light absorbed by a liquid retained by the collapsible reservoir, wherein the liquid comprises an active compound formulation and an excipient, and wherein the excipient is present in an excipient concentration governing a linear relationship between distance and light absorption at a preselected wavelength.

FIG. 4 depicts a schematic view of an exemplary intrathecal pump device electronic module configured with a volumetric assessment engine (VAE) designed to determine a distance separating a light emitter from a light sensor across a collapsible reservoir interior, wherein the distance is determined based on the amount of emitted light absorbed by a liquid retained by the collapsible reservoir, wherein the liquid comprises an active compound formulation and an excipient, and wherein the excipient is present in an excipient concentration governing a linear relationship between distance and light absorption at a preselected wavelength. In FIG. 4, the block diagram of the exemplary intrathecal pump device 110 electronic module includes the computer processor 200 and the computer memory 205. As used herein the term computer processor is synonymous with and interchangeable with the term processor or the term central processing unit (CPU). The processor 200 may comprise two or more computer processors. In the depicted implementation, processor 200 is in electrical communication with computer memory 205. As used herein the term computer memory is synonymous with and interchangeable with the term electronic memory or the term memory. The processor 200 may be operably coupled with the memory 205. The processor 200 may be operably coupled with the memory via a communication network. One or more processors 200 may be operably coupled with one or more memory 205. In the depicted implementation memory 205 includes the program memory 400 and the data memory 405. In the depicted implementation the program memory 400 comprises processor-executable program instructions implementing the volumetric assessment engine (VAE) 115. The data memory 405 may comprise data such as, for example, configuration data, calculation data, reference data, or calibration data resulting from or governing the operation of one or more intrathecal pump device 110 operations or features disclosed herein. The illustrated program memory 400 may include processor-executable program instructions configured to implement an Operating System (OS). The OS may include processor executable program instructions configured to implement various operations when executed by processor 200. The OS may be omitted. The illustrated program memory 400 may include processor-executable program instructions configured to implement various Application Software. The Application Software may include processor executable program instructions configured to implement various operations when executed by processor 200. The Application Software may be omitted.

In the depicted implementation, processor 200 is communicatively and operably coupled with the storage medium 410. The storage medium 410 may be configured to implement various data storage and data retrieval operations for the processor 200 such as for example, read/write, read/only or non-volatile storage and retrieval. Useful examples of the storage medium 410 include but are not limited to, electronic memory, solid state memory, disk storage, flash memory or dynamic memory.

In the depicted implementation, the processor 200 is communicatively and operably coupled with the user interface 415. In various implementations, the user interface 415 may be adapted to receive input from a user or send output to a user. In some implementations, the user interface 415 may be adapted to an input-only or output-only user interface mode. In various implementations, the user interface 415 may include an imaging display. In some embodiments, the user interface 415 may include an audio interface. In some designs, the audio interface may include an audio input. In various designs, the audio interface may include an audio output. In some implementations, the user interface 415 may be touch-sensitive. The user interface 415 may be configured to receive graphical input to the intrathecal pump device 110 electronic module. The graphical input may be drawn using a stylus or a user's finger, in contact with a touch-sensitive surface. The graphical input may be, for example, user input selecting or identifying one or more threshold volumes on a visible model of a collapsible reservoir presented to a user via a graphical display. For example, the visible model may be presented to the user with graduated volume markings. The user may identify a threshold volume for triggering a volume alert by selecting or highlighting one or more graduated volume marking on the visible model. The processor 200 may use the threshold volume selected or identified by the user on the visible model to configure a threshold volume that may trigger volume alerts if the threshold is satisfied by the remaining therapeutic fluid volume in the reservoir. The graphical input may be, for example, user input selecting or identifying location points of light emitters or light sensors in a collapsible reservoir, in a calibration mode. The processor 200 may use the location points of light emitters or light sensors in the collapsible reservoir to calculate light absorption path lengths and distances at different points and through different paths across the collapsible reservoir, in accordance with the techniques disclosed herein. In some designs, the intrathecal pump device 110 electronic module may include an accelerometer operably coupled with the processor 200. In various embodiments, the intrathecal pump device 110 electronic module may include a GPS module operably coupled with the processor 200. In an illustrative example, the intrathecal pump device 110 electronic module may include a magnetometer operably coupled with the processor 200. In some embodiments, the user interface 415 may include an input sensor array. In some embodiments, the input sensor array may include electrical or electronic signal sensing circuitry subsystems or modules configurable by the processor 200 to be adapted to implement operations, such as for example, providing signal input capability, signal output capability, signal sampling, spectral analysis, correlation, autocorrelation, Fourier transforms, buffering, filtering operations including adjusting frequency response and attenuation characteristics of spatial domain and frequency domain filters, signal or waveform recognition, pattern recognition, or anomaly detection. In various implementations, the depicted memory 205 may contain processor executable program instruction modules configurable by the processor 200 to be adapted to implement operations, such as for example, providing signal input capability, signal output capability, signal sampling, spectral analysis, correlation, autocorrelation, Fourier transforms, buffering, filtering operations including adjusting frequency response and attenuation characteristics of spatial domain and frequency domain filters, signal or waveform recognition, pattern recognition, or anomaly detection. In some embodiments, the input sensor array may include electrical or electronic audio sensing circuitry subsystems or modules configurable by the processor 200 to be adapted to provide audio input capability, audio output capability, audio sampling, spectral audio analysis, correlation, autocorrelation, Fourier transforms, audio buffering, audio filtering operations including adjusting frequency response and attenuation characteristics of temporal domain and frequency domain filters, audio pattern recognition, or anomaly detection. In various implementations, the depicted memory 205 may contain processor executable program instruction modules configurable by the processor 200 to be adapted for use with the user interface 415 to provide audio input capability, audio output capability, audio sampling, spectral audio analysis, correlation, autocorrelation, Fourier transforms, audio buffering, audio filtering operations including adjusting frequency response and attenuation characteristics of temporal domain and frequency domain filters, audio pattern recognition, or anomaly detection. The user interface 415 may be implemented in a mobile device operably coupled with the processor 200. For example, the user interface 415 may be configured in the mobile device 125 depicted at least by FIG. 1.

In the depicted implementation, processor 200 is communicatively and operably coupled with the Input/Output (I/O) interface 210. In the depicted implementation, the I/O interface 210 includes the sensor interface 420. The sensor interface 420 may be configurable to receive sensor signals from one or more sensors configured to measure received light. The sensor interface 420 may be configurable to provide the processor 200 access to sensor information comprising illuminance values for each of the one or more sensors operably coupled with the sensor interface 420. The illuminance values may be measured in lux (lumens per square meter). The sensor information received from the one or more sensors by the sensor interface 420 or provided to the processor 200 may be any measure of received light intensity that would be known to one of ordinary skill. The sensor information may be received by the sensor interface 420 using one or more wired or wireless interfaces operably coupled with one or more light sensors. The sensor interface 420 may be configurable to operably connect to one or more light sensor types. The sensor interface 420 may be configurable to receive input from one or more light sensor types, including but not limited to photoresistors, photodiodes, phototransistors, and photovoltaic light sensors. The sensor interface 420 may receive an input signal from a light sensor operably coupled with the sensor interface 420. The sensor interface 420 may receive one or more input signals from one or more light sensors. The one or more input signals received by the sensor interface 420 from the one or more light sensors may comprise information representative of the light intensity incident on or received by the one or more light sensors. One or more input signals received by the sensor interface 420 may be an analog signal. One or more input signal received by the sensor interface 420 may be a digital signal. The digital signal received by sensor interface 420 may be, for example, a digital representation of light intensity received by a light sensor. The digital representation of light intensity received by a light sensor may comprise a number having a value on a scale of numbers in a range representing light intensities, from a minimum light intensity when the light sensor is in darkness to a maximum light intensity when the light sensor is saturated with light. The analog signal received by sensor interface 420 may be, for example, an analog voltage or current representation of light intensity received by a light sensor. The analog representation of light intensity may be, for example, a voltage or current value on a scale representing a minimum light intensity when the light sensor is in darkness to a maximum light intensity when the light sensor is saturated with light. Sensor interface 420 may be configured to use an analog-to-digital converter (ADC) to convert an analog signal from one or more light sensors to one or more digital signal. The sensor interface 420 may be configurable by processor 200 to implement any of the disclosed features or operations.

In the depicted implementation, the I/O interface 210 includes the emitter interface 425. The emitter interface 425 may be configurable to activate one or more light emitters to emit light. The emitter interface 425 may comprise one or more wired or wireless interfaces configured to be operably coupled with one or more light emitters. The one or more light emitter operably coupled with the emitter interface 425 may be, for example, a light emitting diode (LED), a laser diode (LASD) or any type of light emitter that would be known to one of ordinary skill. The emitter interface 425 may be configurable to individually activate one or more light emitters to emit light. The emitter interface 425 may be configurable to selectively activate one or more light emitters of multiple light emitters to emit light. From a group or set comprising multiple light emitters, the emitter interface 425 may be configurable to selectively activate some light emitters to emit light and refrain from activating other light emitters to not emit light and remain dark. The emitter interface 425 may be configurable to change the state of any light emitter operably coupled with the emitter interface 425. For example, the emitter interface 425 may be configurable to activate or turn on any light emitter causing the light emitter to emit light. The emitter interface 425 may be configurable to deactivate or turn off any light emitter causing the light emitter to not emit light and be or remain dark. The emitter interface 425 may be configurable to operably connect to one or more light emitter types. For example, the emitter interface 425 may be configurable to control multiple light emitter packages wherein each individual light emitter package is configured with multiple emitters designed to emit light at different wavelengths or different colors. For example, the emitter interface 425 may be configurable to independently drive individual light emitters of a multi-color light emitter package to individually and selectively activate and deactivate light emitters of different colors or wavelengths, one at a time or more than one at a time. Configuring the emitter interface 425 to individually and selectively activate and deactivate light emitters of different colors or wavelengths, one at a time or more than one at a time may permit emitting mixed color or mixed wavelength light mixed from multiple light emitters. Emitting mixed wavelength light from multiple light emitters, at the same time or one at a time, may permit more accurate light absorption-based distance measurements through mixtures of fluids having multiple distinct absorption spectra. Measuring light absorption through mixtures of fluids having multiple distinct absorption spectra may permit more accurate identification of mixture component concentrations, based on comparing measured and actual light absorption through the mixture for each wavelength with an expected absorption for each mixture component. The emitter interface 425 may be configurable to activate an LED designed to emit light having a broad spectrum at the same time as an LED configured to emit light having a narrower spectrum. Combining broad spectrum light emitted at the same time as light having a narrower spectrum may permit more accurate measurements of transmission medium material properties. Emitting one or more narrow spectrum lights at the same time as a broader spectrum light may permit more accurate distance measurements through a transmission medium based on different medium material absorption characteristics for each different wavelength of multiple narrow spectrum lights. For example, multiple narrow spectrum light emitters may be selectively activated to make distance-based light absorption measurements through a medium having a mixture of materials each present in a distinct concentration. In an illustrative example, each different narrow spectrum light of a group of multiple narrow spectrum lights may be selected to emit light having a wavelength with specific absorption characteristics in particular materials. The emitter interface 425 may be configurable to drive one or more light emitters operably coupled with the emitter interface using pulse width modulation (PWM) techniques as would be known to one of ordinary skill. The emitter interface 425 may be configurable with PWM parameters, for example pulse width, amplitude, rise and/or fall time, repetition rate or duty cycle. Configuring the emitter interface 425 with PWM parameters may permit driving one or more light emitters using PWM techniques to dim or vary intensity of light emitted by the one or more light emitters. The emitter interface 425 may be configurable to adjust electric current flowing in one or more light emitters operably coupled with the light emitter interface 425. Configuring the emitter interface 425 to adjust electric current flowing in one or more light emitters may permit controlling the brightness or amount of light emitted by the one or more light emitters. The emitter interface 425 may be configured to use a digital-to-analog converter (DAC) to convert a digital signal from the processor 200 to an analog signal to drive one or more light emitters. The emitter interface 425 may be configurable by processor 200 to implement any of the disclosed features or operations.

In the depicted implementation, the I/O interface 210 includes the pump interface 430. In the depicted implementation the pump interface 430 includes electronic circuitry designed to power and control a pump adapted to deliver therapeutic fluid. The pump may be a peristaltic pump. The pump interface 430 may be configurable to power and control a constant rate peristaltic pump designed to deliver therapeutic fluid at a constant rate. The pump interface 430 may be configurable to power and control a variable rate peristaltic pump designed to deliver therapeutic fluid at a rate programmed by the processor 200. The pump interface 430 may be configurable by processor 200 to implement any peristaltic pump features or operation modes available and as would be known to one of ordinary skill.

In the depicted implementation, the processor 200 is communicatively and operably coupled with the communication interface 215. In the depicted implementation, the communication interface 215 includes a network interface. The network interface may be a wireless network interface. The wireless interface may be configured to transmit and/or receive communication signals using the antenna 240, depicted at least by FIG. 2. In some designs, the network interface may be a Wi-Fi™ interface. The network interface may be a BLUETOOTH interface. In an illustrative example, the intrathecal pump device 110 electronic module may include more than one network interface. The network interface may be a wireline interface. The network interface may be omitted.

Useful examples of the illustrated intrathecal pump device 110 electronic module include, but are not limited to, embedded systems or other personal, wearable, or implantable computing devices as would be known to one of ordinary skill. In some implementations, multiple intrathecal pump device 110 electronic module devices may be operably linked to form a network of intrathecal pump device 110 electronic modules in a manner as to distribute and share one or more resources. For example, a network of intrathecal pump device 110 electronic modules may be linked with clustered computing devices and server banks/farms hosting cloud-based machine learning or artificial intelligence models configured to make predictions such as, for example, therapeutic fluid flow rates and/or refill schedules optimal for a patient, predicted as a function of collapsible reservoir volume over time. In some embodiments, an exemplary intrathecal pump device 110 electronic module design may be realized in a distributed implementation. An intrathecal pump device 110 electronic module design may be partitioned between a client device, such as, for example, an embedded processor implant, and a more powerful server system with greater resources, such as for example, computation, memory, or storage capacity. In various designs, a intrathecal pump device 110 electronic module partition hosted on a PC or mobile device may choose to delegate some parts of computation, such as, for example, machine learning or deep learning, to another more powerful host server. In some embodiments, a client device partition may delegate computation-intensive tasks to a host server to take advantage of a more powerful processor, or to offload excess work. In an illustrative example, some intrathecal pump device 110 implementations may be configured to offload computation to a cloud server configured with a graphics processing unit (GPU) including an engine adapted to implement specialized processing, such as, for example, neural networks, machine learning, artificial intelligence, image recognition, audio processing, or digital signal processing. In some embodiments, such a cloud-hosted engine adapted to specialized processing may add processing power sufficient to implement intrathecal pump device 110 electronic module features on a low-power implantable device.

Figure 5:
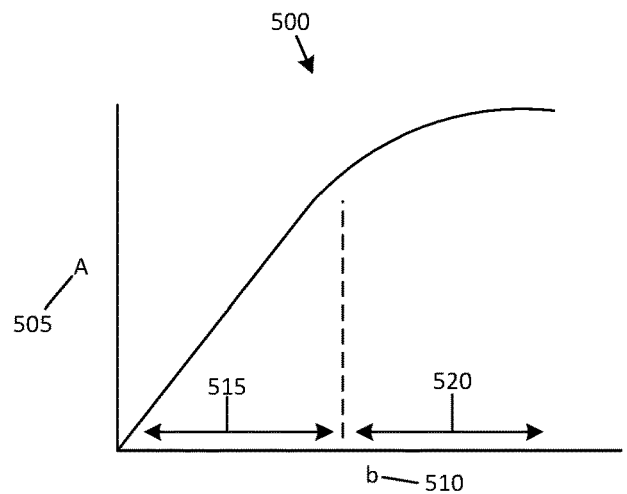
FIG. 5 is a graph depicting exemplary absorption (A) as a function of distance (b) for methylene blue.

FIG. 5 is a graph depicting exemplary absorption (A) as a function of distance (b) for methylene blue. In FIG. 5, the exemplary excipient light absorption response 500 for methylene blue as the absorbing agent obeys Beer's law. Beer's law relates light absorption (A) 505 by a medium (for example a liquid) to an absorption coefficient (a) of the medium for a particular light wavelength, the thickness/distance (b) light travels through the medium and the absorbing agent concentration (c), by A=abc. Beer's law may be used to measure variable concentration when distance (b) is constant. However, the present disclosure teaches application of Beer's law to measure variable thickness of a collapsible reservoir with an absorbing agent concentration (c) chosen so that the relationship between (A) and (c) is in the linear region. In FIG. 5, the excipient light absorption response 500 shows absorption A 505 as a function of distance b 510 and a concentration (c) of methylene blue. In an illustrative example, fluorescein emission is proportional to reservoir length as governed by Beer's law, and measurement techniques taught herein apply. One of ordinary skill would recognize the absorbing agent may be fluorescein, or any absorbing agent that obeys Beer's law. In the example depicted by FIG. 5, the absorbing agent concentration (c) governs the linearity of the relationship between (A) and (c). In the example depicted by FIG. 5, the absorbing agent concentration (c) in the linear region 515 governs a linear relationship between (A) and (c). Higher absorbing agent concentration (c) in the non-linear region 520 changes absorptivity and/or changes the refractive index because of increased particle interactions. Choosing an absorbing agent concentration (c) so that the relationship between (A) and (c) is in the linear region 515, measuring absorption A 505 and holding (a) and (c) constant permits straightforward calculation of the distance b=A/(ac).

Figure 6A:
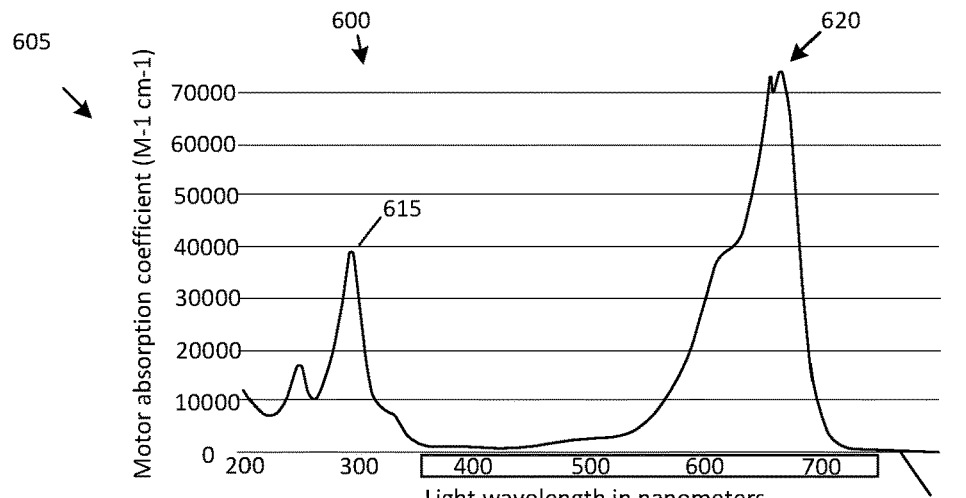
FIG. 6A is a graph depicting an exemplary absorption spectrum of methylene blue.

FIG. 6A is a graph depicting an exemplary absorption spectrum of methylene blue. In FIG. 6A, the exemplary excipient light absorption spectrum 600 shows the excipient molar light absorption coefficient 605 as a function of light wavelength 610 with methylene blue as the absorbing agent. The excipient molar light absorption coefficient 605 is the absorption coefficient (a) described with reference to FIG. 5 for the light wavelength 610. In the example depicted by FIG. 6A the excipient molar light absorption coefficient 605 has a local maximum 615 at about 300 nm and a global maximum 620 at about 660 nm.

Figure 6B:
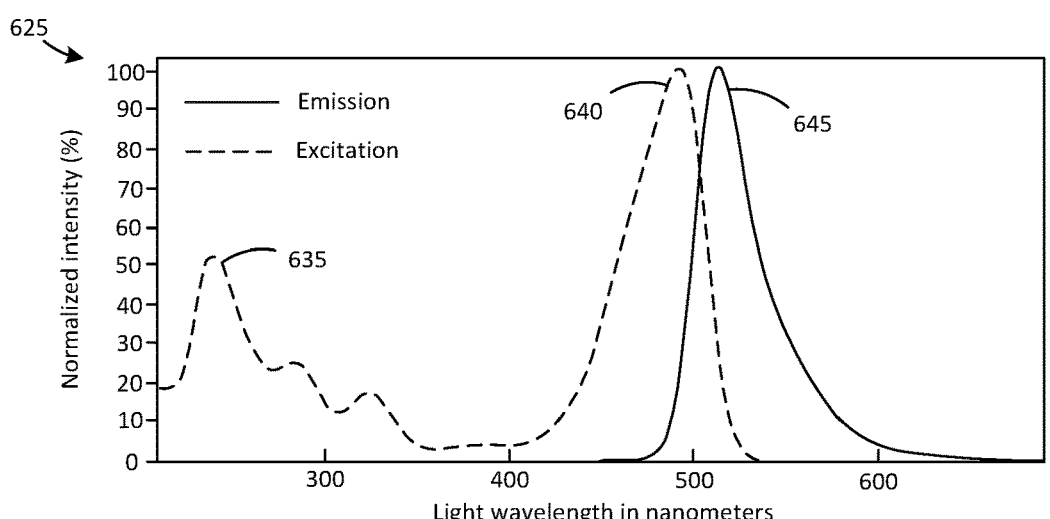
FIG. 6B is a graph depicting exemplary emission and excitation spectra of fluorescein.

FIG. 6B is a graph depicting exemplary emission and excitation spectra of fluorescein. Fluorescein is used in several clinical applications: topically (ophthalmic), intravenously (fluorescence angiography). FIG. 6B depicts the normalized intensity 625 of fluorescein as a function of light wavelength 630. In the example depicted by FIG. 6B, the fluorescein excitation spectrum normalized intensity has a local peak 635 near 100 nm. In the example depicted by FIG. 6B, the fluorescein excitation spectrum normalized intensity has a global peak 640 near 490 nm. In FIG. 6B the depicted fluorescein emission spectrum normalized intensity shows a global peak at about 520 nm. Fluorescein may be used to detect a CSF leak after intrathecal catheter placement. Fluorescein may be administered through the catheter and leaking may be detected by UV light. Accordingly, there is clinical precedent for fluorescein administration into the intrathecal space. An implementation in accordance with the present disclosure may be configured to use fluorescein as an excipient. For example, in commercial settings UV (black) light of around 350 nm may be used to excite fluorescein to emit wavelengths with a peak at 520 nm. UV light makes the fluorescein appear to glow at a green/yellow color. An implementation in accordance with the present disclosure may be configured with a light emitter (for example an emitting LED) having a wavelength appropriate for fluorescein excitation, such as approximately 350 to 365 nm. Such an implementation configured to use fluorescein as an excipient may be configured with a light sensor having highest sensitivity in the 520 nm range. Such an implementation may advantageously choose some distance between wavelengths to avoid too much crosstalk at the light sensor. In any case, fluorescein emission at 520 nm is proportional to reservoir length as governed by Beer's law, and measurement techniques taught herein apply.

Figure 7:
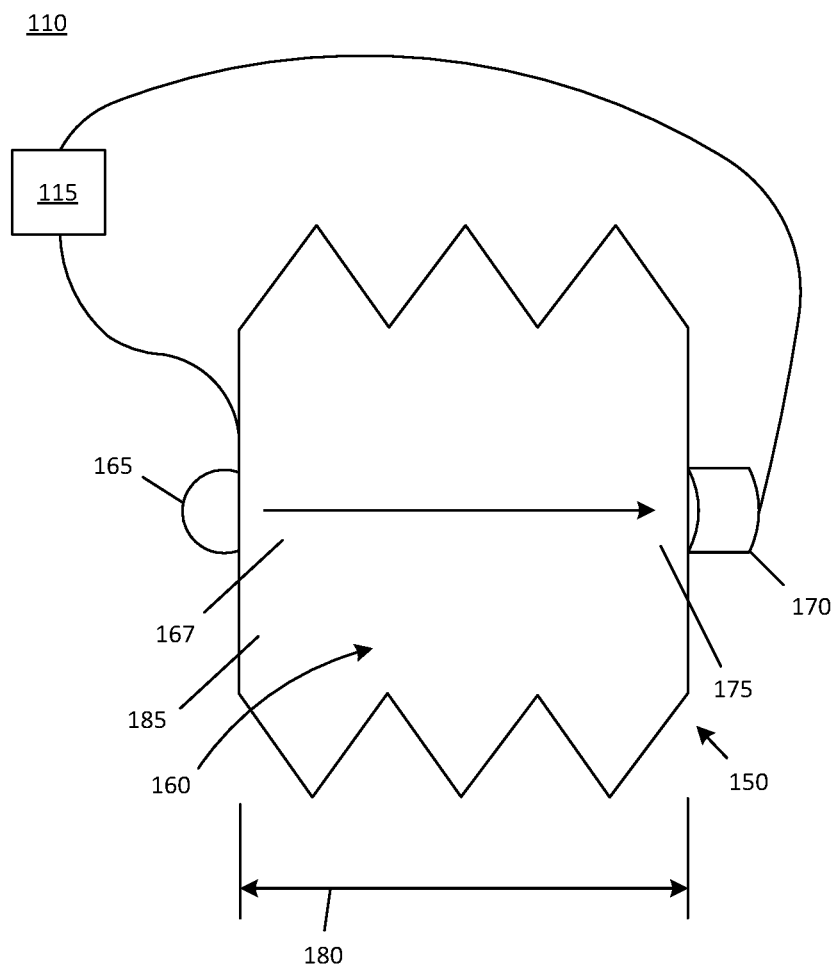
FIG. 7 depicts an exemplary volume assessment implementation configured to determine a distance separating a light emitter from a light sensor across a collapsible reservoir interior based on the amount of emitted light absorbed by a liquid retained by the collapsible reservoir and determine the volume of the liquid retained by the collapsible reservoir based on the distance.

FIG. 7 depicts an exemplary volume assessment implementation configured to determine a distance separating a light emitter from a light sensor across a collapsible reservoir interior based on the amount of emitted light absorbed by a liquid retained by the collapsible reservoir and determine the volume of the liquid retained by the collapsible reservoir based on the distance. In FIG. 7, the exemplary intrathecal pump device 110 is configured to use a photometric method to assess real-time volume of the collapsible reservoir 150. In the depicted implementation the VAE 115 activates the light emitter 165 to direct emitted light 167 from one side of the collapsible reservoir 150 to the light sensor 170 on another side of the collapsible reservoir 150. The light emitter 165 may be a light emitting diode (LED) diode designed to emit light of a selected wavelength. The light emitter 165 may be a Red LED designed to emit light having a wavelength of approximately 660 nm. The emitted light 167 from the light emitter 165 passes through the liquid 185 retained by the collapsible reservoir 150. In the depicted implementation the liquid 185 is a therapeutic fluid. In the depicted implementation an excipient has been added to the therapeutic fluid. In the depicted implementation the excipient is a dye with a predetermined absorption characteristic at the selected frequency of light. In the depicted implementation the excipient is present in the therapeutic fluid in the excipient concentration 160. The excipient concentration 160 in the therapeutic fluid has been chosen to govern a linear relationship between distance 180 and light absorption 175 at the preselected wavelength. In the depicted implementation the source light intensity, $I_o$, of the emitted light 167 from the light emitter 165 is attenuated by light absorption 175 as the emitted light 167 passes through the liquid 185 retained by the collapsible reservoir 150 to reach the light sensor 170. The source light intensity, $I_o$, of the emitted light 167 from the light emitter 165 may be measured during a calibration operation. The calibration operation may measure the source light intensity $I_o$ through a test medium having a known absorption characteristic. The source light intensity, $I_o$, of the emitted light 167 from the light emitter 165 may be estimated using manufactured specification data for the light emitter 165 and/or control parameters applied to the light emitter 165 such as current, voltage or PWM modulation characteristics.

The light sensor 170 may be a photoresistor. The light sensor 170 may be on a side of the collapsible reservoir 150 opposite from the light emitter 165. VAE 115 receives a signal from the light sensor 170 representing the intensity of light that reached the light sensor 170. VAE 115 uses the signal received from the light sensor 170 to measure the intensity, I of light received by the light sensor 170. The received light intensity I is the light intensity received by the light sensor 170 through the liquid 185. In the depicted implementation, the distance 180 the emitted light 167 must travel before reaching the light sensor 170 on the opposite side of the collapsible reservoir 150 from the light emitter 165 varies directly with reservoir volume. That is, as the liquid 185 within the collapsible reservoir 150 is depleted, the collapsible reservoir 150 collapses and the distance 180 between the two sides decreases. According to Beer's Law, as the distance 180 between the two sides decreases, light absorption 175 decreases and less light is absorbed. In the depicted implementation VAE 115 calculates the light absorption 175 using the source light intensity, $I_o$, and the light intensity received by the light sensor 170, I, as $A=\ln(I_o/I)$. With the excipient concentration 160 (that is, the absorbing agent concentration (c)) chosen to govern a linear relationship between (A) and (c), holding (a) and (c) constant permits straightforward calculation of the distance $b=A/(ac)$.

In the depicted implementation VAE 115 calculates the volume of liquid 185 remaining in the collapsible reservoir 150 using the distance 180 and the predetermined geometric characteristics of the collapsible reservoir 150. For example, in the illustrated example, the collapsible reservoir may be modeled as a box structure with a variable height defined by the distance 180. Other structure models may be used to derive volume calculations as would be known to one of ordinary skill. The implementations disclosed herein present a 2-dimensional reservoir, however the volume calculations may be extrapolated to a 3-dimensional reservoir. Because the excipient concentration 160 comprising the dye added to the liquid 185 is selected so that the relationship between distance 180 and light absorption 175 is linear, this photometric method provides a 'real-time' assessment of reservoir volume with improved accuracy. In some implementations the VAE 115 may store and/or send electronic data representing the volume of liquid 185 remaining in the collapsible reservoir 150. In some designs the implementation depicted by FIG. 7 may assume the two flat ends will remain parallel to each other as collapsible reservoir 150 collapses. However, in some scenarios the two flat ends may not remain parallel to each other as collapsible reservoir 150 collapses, resulting in a non-parallel reservoir collapse. In an illustrative example, collapsible reservoir 150 may be an accordion reservoir configured with folds that may compress at varying rates, causing a non-parallel reservoir collapse. The Applicant has devised light emitter 165 and light sensor 170 configurations designed to achieve accurate volume measurement in non-parallel reservoir collapse scenarios and permit more accurate assessment of reservoir volume even if sides remain substantially parallel. These designs encompass scaling of and/or slightly more complex arrangement of components and are disclosed with reference to FIGS. 8 and 10-12.

Figure 8:
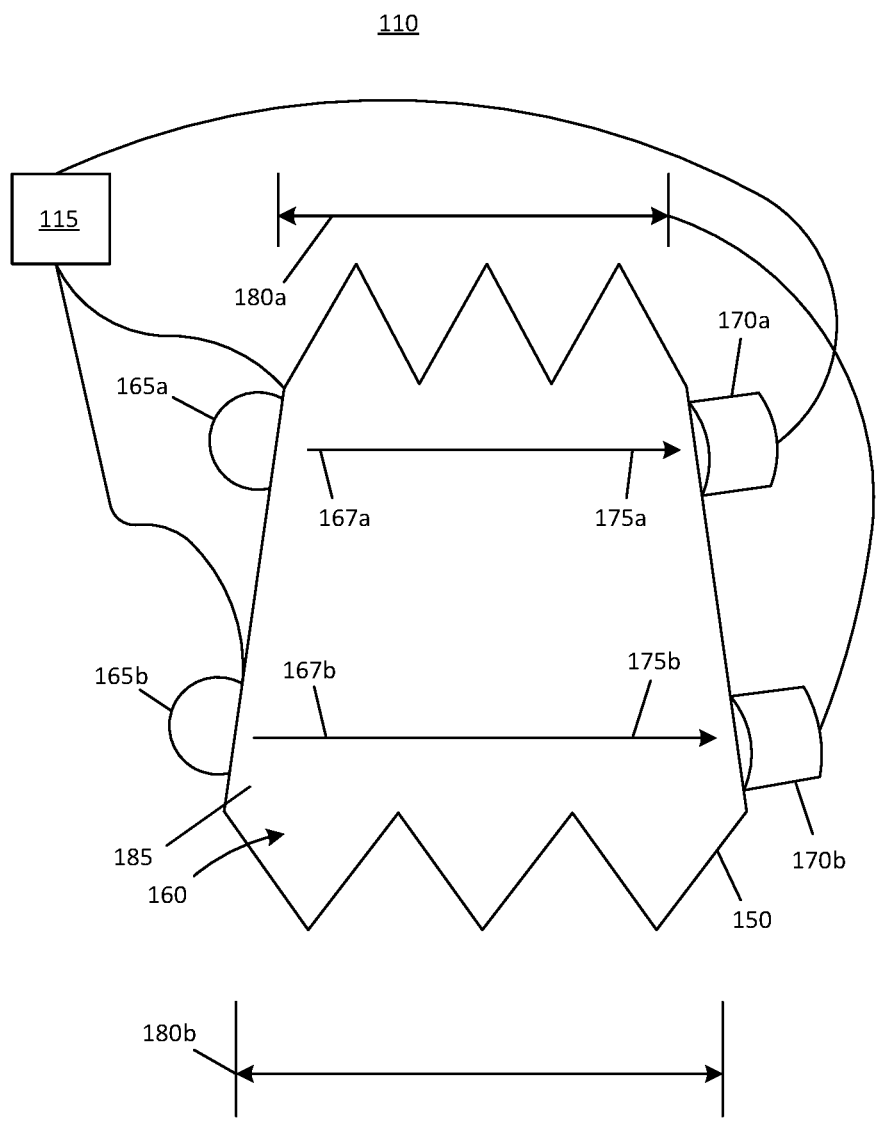
FIG. 8 depicts an exemplary volume assessment implementation configured to determine a distance across a collapsible reservoir interior using at least two light emitters and at least two light sensors to achieve more accurate volume measurements in non-parallel reservoir collapse scenarios.

FIG. 8 depicts an exemplary volume assessment implementation configured to determine a distance across a collapsible reservoir interior using at least two light emitters and at least two light sensors to achieve more accurate volume measurements in non-parallel reservoir collapse scenarios. The example depicted by FIG. 8 comprises the intrathecal pump device 110 features disclosed with reference to at least FIG. 7. The exemplary intrathecal pump device 110 depicted by FIG. 8 is configured to use a photometric method to assess real-time volume of the collapsible reservoir 150 in a non-parallel collapse scenario, based on measuring or calculating multiple distances or reservoir thicknesses using multiple measurements of light absorption across the collapsible reservoir 150. The measured or calculated distance or reservoir thickness may be an average distance or reservoir thickness determined as a function of multiple measurements of light absorption in different paths through liquid retained by the collapsible reservoir 150. The intrathecal pump device 110 depicted by FIG. 8 is configured with multiple light emitters 165a,b and multiple light sensors 170a,b permitting the VAE 115 to obtain multiple measurements of light absorption 175a,b using different paths through the liquid 185. In FIG. 8 the VAE 115 activates the light emitter 165a to direct emitted light 167a to light sensor 170a and the VAE 115 activates the light emitter 165b to direct emitted light 167b to light sensor 170b. The emitted light 167a is attenuated by the light absorption 175a as the emitted light 167a passes through the liquid 185. The emitted light 167b is attenuated by the light absorption 175b as the emitted light 167b passes through the liquid 185. In the depicted implementation VAE 115 measures the light absorption 175a,b using the light sensors 170a,b. VAE 115 uses the light absorption measurements 175a,b to determine the distances 180a,b. In the implementation depicted by FIG. 8 the VAE 115 calculates the average reservoir distance or thickness of the reservoir 150 and the volume of remaining liquid 185, as a function of the distances 180a,b based on the techniques disclosed at least with reference to FIG. 7. Although the implementation depicted by FIG. 8 is disclosed using two light emitters 165a,b and two light sensors 170a,b the disclosed techniques may be extended to any number of light emitters 165 and light sensors 170. In an illustrative example, an intrathecal pump device 110 implemented using a cylindrical reservoir may be configured with at least three light emitter 165 and light sensor 170 pairs. The example depicted by FIG. 8 discloses one technique to achieve more accurate remaining liquid volume measurement in a non-parallel reservoir collapse scenario. In some scenarios, cross-interaction between light emitter 165 and light sensor 170 pairs may result in undesirable crosstalk, depicted in FIG. 9.

Figure 9:
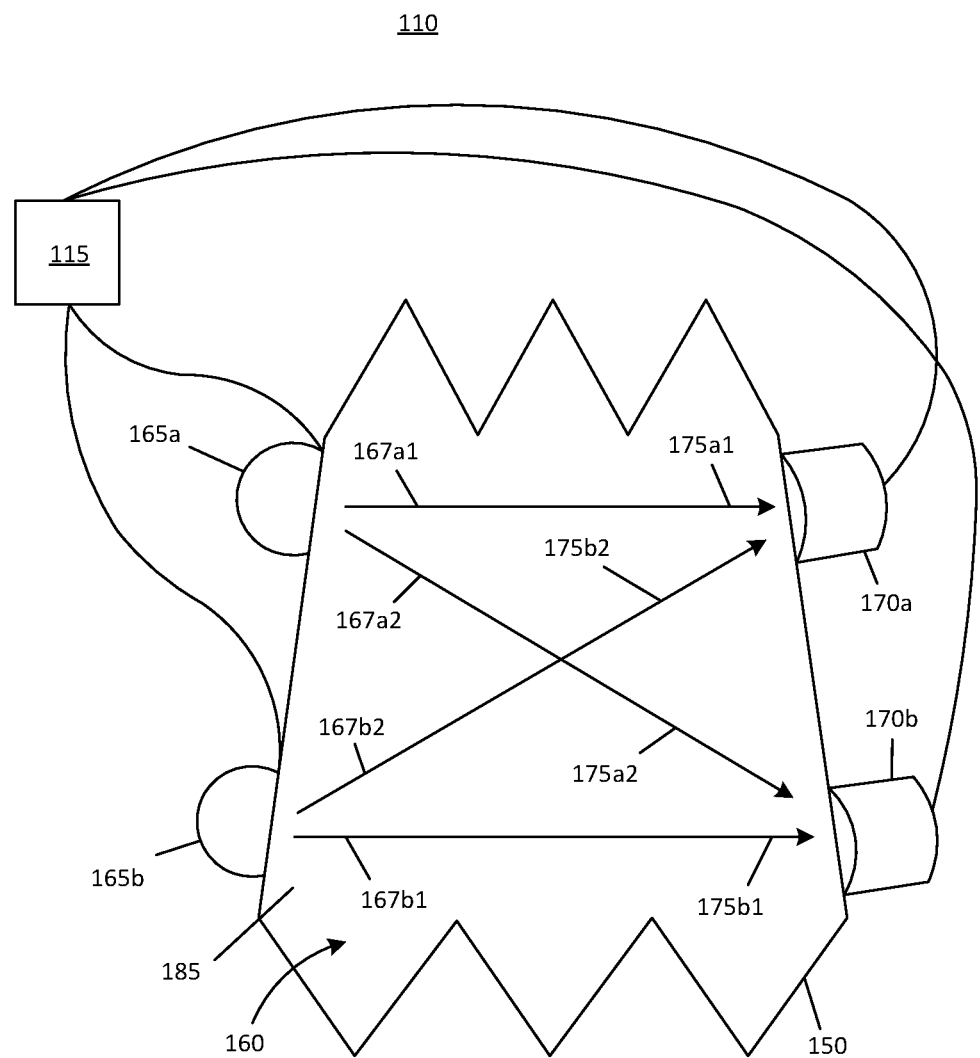
FIG. 9 depicts exemplary undesirable crosstalk between emitter/sensor pairs that may be encountered using at least two light emitters and at least two light sensors to determine a distance across a collapsible reservoir interior.

FIG. 9 depicts exemplary undesirable crosstalk between emitter/sensor pairs that may be encountered using at least two light emitters and at least two light sensors to determine a distance across a collapsible reservoir interior. In FIG. 9, the VAE 115 activates the light emitter 165a to direct emitted light 167a1 to light sensor 170a and the VAE 115 activates the light emitter 165b to direct emitted light 167b1 to light sensor 170b. In the example depicted by FIG. 9 the light emitter 165a and the light emitter 165b emit non-laser light that also scatters in solutions such as the liquid 185 retained by the collapsible reservoir 150. In the example depicted by FIG. 9, the light emitter 165a directs emitted light 167a1 to the light sensor 170a. Emitted light 167a1 is attenuated by light absorption 175a1. The emitted light 167a1 from light emitter 165a scatters in liquid 185. The scattered light from light emitter 165a reaches the light sensor 170b as emitted light 167a2 attenuated by light absorption 175a2. In the example depicted by FIG. 9, the light emitter 165b directs emitted light 167b1 to the light sensor 170b. Emitted light 167b1 is attenuated by light absorption 175b1. The emitted light 167b1 from light emitter 165b scatters in liquid 185. The scattered light from light emitter 165b reaches the light sensor 170a as emitted light 167b2 attenuated by light absorption 175b2. In the example depicted by FIG. 9, cross-interaction between light emitter 165a,b and light sensor 170a,b pairs results in undesirable crosstalk from light scattered by passing through the liquid 185, so that light from each light emitter 165 will be received by more than one light sensor 170. Such undesirable crosstalk between light emitter 165 and light sensor 170 pairs may cause loss of accuracy in distance and volume measurement. In an illustrative example, measured light absorption may be lower than actual light absorption as a result of additive scattered light received by each light sensor 170 from each light emitter 165. The Applicant has devised light emitter 165 and light sensor 170 configurations with VAE 115 implementations designed to avoid measurement inaccuracy resulting from undesirable crosstalk. An exemplary implementation configured to avoid measurement inaccuracy resulting from undesirable crosstalk is described with reference to FIGS. 10 and 11.

Figure 10:
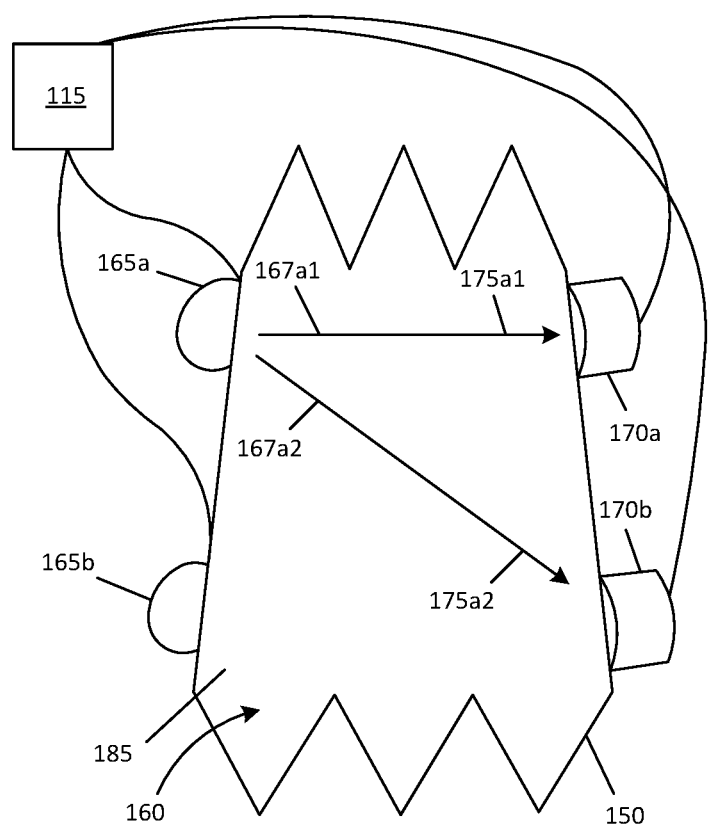
FIG. 10 and FIG. 11 depict aspects of an exemplary volume assessment implementation configured to mitigate the crosstalk between emitter/sensor pairs depicted by FIG.
Figure 11:
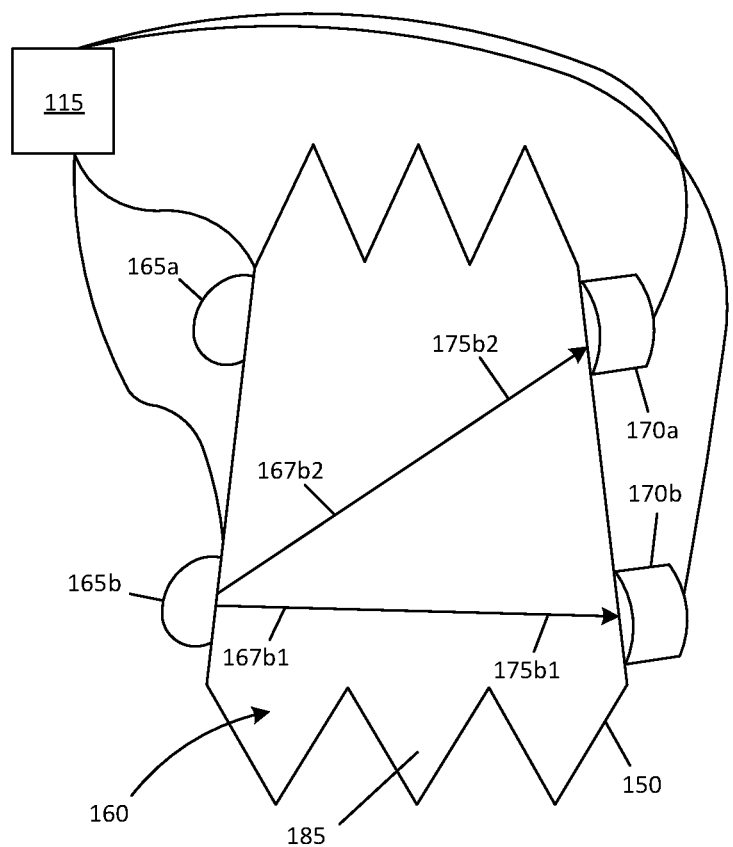

FIG. 10 and FIG. 11 depict aspects of an exemplary volume assessment implementation configured to mitigate the crosstalk between emitter/sensor pairs depicted by FIG. 9, based on cycling activation of at least two light emitters through at least two respective on and off time periods. The example depicted by FIGS. 10 and 11 comprise the intrathecal pump device 110 features disclosed with reference to at least FIGS. 7 and 8. In FIGS. 10 and 11 the exemplary intrathecal pump device 110 is configured with VAE 115 implemented with processor executable program instructions designed to alternate on/off times of each light emitter 165a,b, permitting the VAE 115 to compensate for crosstalk. By alternating on/off times of each light emitter 165a,b the VAE 115 may measure light absorptions at each light detector 170a,b from each light emitter 165a,b. In an illustrative example, measuring light absorptions at each light detector 170a,b from each light emitter 165a,b may permit the VAE 115 to cancel crosstalk that may result if light from each light emitter 165a,b is received by more than one light sensor 170a,b.

In the example depicted by FIGS. 10 and 11 VAE 115 may be configured to cycle each light emitter 165a,b through a respective on and off sequence. The respective on and off sequence for each light emitter 165a,b may comprise a light emitting time period and a dark time period for each light emitter 165a,b. In the implementation depicted by FIGS. 10 and 11, FIG. 10 shows one light emitting time period for the light emitter 165a. During the light emitting time period when light emitter 165a is on shown by FIG. 10, light emitter 165b shown in FIG. 11 is off. FIG. 11 shows another light emitting time period for the light emitter 165b. During the light emitting time period when light emitter 165b is on shown in FIG. 11, light emitter 165a shown in FIG. 10 is off. Although the implementation depicted by FIGS. 10 and 11 is disclosed using two light emitters 165a,b and two light sensors 170a,b the disclosed techniques may be extended to any number of light emitters 165 and light sensors 170.

Cycling each light emitter 165a,b of at least two light emitters 165a,b through respective on and off sequences causes each light emitter 165a,b to transmit emitted light 167 from one light emitter 165a,b at a time. In an illustrative example, cycling rates may be relatively low at least because ambient light should not be a problem for light sensors inside the implanted reservoir. The emitted light 167 is transmitted from one light emitter 165a,b at a time through the liquid 185 retained by a collapsible reservoir 150 to at least two light sensors 170a,b disposed in the collapsible reservoir 150. In FIG. 10, light emitter 165a directs light to light sensor 170a during an activation time period for light emitter 165a when light emitter 165b is off. Liquid 185 disperses light from light emitter 165a causing scattered light to reach light sensor 170b. The scattered light received by light sensor 170b is a lower intensity because of a longer path and dispersion through the liquid. In FIG. 11, light emitter 165b directs light to light sensor 170b during an activation time period for light emitter 165b when light emitter 165a is off. Liquid 185 disperses light from light emitter 165b causing scattered light to reach light sensor 170a. The scattered light received by light sensor 170a is a lower intensity because of a longer path and dispersion through the liquid 185.

In the example depicted by FIGS. 10 and 11, VAE 115 may be configured to determine a sum amount of emitted light 167 received by the at least two light sensors 170 in various ways. VAE 115 may use the sum amount of emitted light to determine light absorption across the collapsible reservoir. VAE 115 may use light absorption to determine the distance across the collapsible reservoir.

For example, VAE 115 may be configured to determine light absorption based on a sum, of emitted light received by light sensor 170a from light emitter 165a during an activation period for light emitter 165a, and emitted light received by light sensor 170b from light emitter 165b during a subsequent activation period for light emitter 170b. VAE 115 may be configured to calculate an average light absorption and distance using the sum of emitted light received by light sensor 170a and light sensor 170b in separate activation periods for respective light emitters 165a and 165b. In an illustrative example the VAE 115 may be configured to read received light intensity information from a light sensor 170a,b disposed substantially opposite the respective light emitter 165a,b. Reading received light intensity information from a light sensor 170 disposed substantially opposite the respective light emitter 165 permits the VAE 115 to avoid inaccuracies resulting from the longer path and increased dispersion through the liquid 185 to light sensors 170 not disposed substantially opposite the activated light emitter 165. VAE 115 may be configured to ignore the received light intensity information from light sensors 170 not disposed substantially opposite the activated light emitter 165.

VAE 115 may be configured with data representing light emitter 165 and light sensor pairs that are substantially opposite from each other across a collapsible reservoir interior. In an illustrative example the VAE 115 may be configured to use the data identifying light emitter 165 and light sensor pairs that are substantially opposite from each other. VAE 115 may sequence activation of light emitters 165 and received light measurement using light sensors 170 identified by the configuration data as substantially opposite a respective light emitter 165. In an illustrative example, VAE 115 may be configured to automatically generate such a light emitter 165 to light sensor 170 physical location correspondence table in a calibration procedure programmed into the VAE 115. For example, VAE 115 may individually activate light emitters 165 one at a time while reading received light intensity information from multiple light sensors 170. The VAE 115 may be configured to identify a light sensor 170 that is substantially opposite a particular light emitter 165 as the light sensor 170 indicating the strongest received light from the particular light emitter 165. In an illustrative example the VAE 115 may generate the light emitter 165 to light sensor 170 physical location correspondence table comprising light emitter 165 and light sensor 170 pairs that are substantially across from each other. For example one entry in the light emitter 165 to light sensor 170 physical location correspondence table may be light emitter 165a and light sensor 170a. Another entry in the light emitter 165 to light sensor 170 physical location correspondence table may be light sensor 165b and light emitter 170b.

For example, as shown by FIG. 10, VAE 115 may be configured to activate light emitter 165a during one light emitting time period to direct light to light sensor 170a. VAE 115 may deactivate or leave dark the light emitter 165b (depicted by FIG. 11) during the light emitting time period for light emitter 165a. VAE 115 may measure light absorption 175a1 using light sensor 170a during the light emitting time period for light emitter 165a. During the same light emitting time period for light emitter 165a VAE 115 may ignore the light absorption 175a2 that would be measurable using light sensor 170b. As shown by FIG. 11, VAE 115 may be configured to activate light emitter 165b during one light emitting time period to direct light to light sensor 170b. VAE 115 may deactivate or leave dark the light emitter 165a (depicted by FIG. 10) during the light emitting time period for light emitter 165b. VAE 115 may measure light absorption 175b1 using light sensor 170b during the light emitting time period for light emitter 165b. During the same light emitting time period for light emitter 165b VAE 115 may ignore the light absorption 175b2 that would be measurable using light sensor 170a.

In an illustrative example, VAE 115 may be configured to activate each light emitter 165 of multiple light emitters 165 one at a time during individual activation times for each light emitter. VAE 115 may be configured to read light intensity information received from each light sensor 170 of multiple light sensors during each of the individual activation times. VAE 115 may be configured to add all of the light intensity information from each light sensor during all of the activation times. VAE 115 may be configured to determine average light absorption based on a sum of the light intensity information from each light sensor during all of the activation times. VAE 115 may be configured to add only the light intensity information from each light sensor that is located substantially opposite a respective light sensor for all of the activation times. In the example depicted by FIGS. 10 and 11, VAE 115 may be configured to determine an average amount of the emitted light 167 received by each light sensor 170 of the at least two light sensors 170 during the at least two light emitting time periods. In the example depicted by FIGS. 10 and 11, the VAE 115 may be configured to determine an average distance 180 across the collapsible reservoir 150 interior. VAE 115 may determine the average distance 180 across the collapsible reservoir 150 interior based on the average amount of emitted light 167 absorbed by liquid 185. VAE 115 may determine the average amount of emitted light 167 absorbed by the liquid 185 as a function of the average amount of the emitted light 167 received by each light sensor 170 of the at least two light sensors 170 during the at least two light emitting time periods.

FIG. 12 depicts an exemplary volume assessment implementation configured to determine a distance across a collapsible reservoir interior using one light emitter and at least two light sensors. The implementation depicted by FIG. 12 comprises the intrathecal pump device 110 features disclosed with reference to at least FIGS. 7 and 8. In FIG. 12, the exemplary intrathecal pump device 110 includes a single light emitter 165 paired with two light sensors 170a,b. Although the implementation depicted by FIG. 12 is disclosed using one light emitter 165 and two light sensors 170a,b the disclosed techniques may be extended to any number of light emitters 165 each associated with two or more light sensors 170. In the implementation depicted by FIG. 12 the light emitter 165 directs light to the light sensors 170a,b. The light emitted from the light emitter 165 takes different paths as emitted light 167a1 and emitted light 167a2 through the liquid 185. Emitted light 167a1 reaches light sensor 170a attenuated by light absorption 175a1. Emitted light 167a2 reaches light sensor 170b attenuated by light absorption 175a2. In the implementation depicted by FIG. 12 the VAE 115 reads received light intensity information from the light sensors 170a,b. In the implementation depicted by FIG. 12 VAE 115 may be configured to determine the average absorption as a function of the sum of absorption measurements by the VAE 115 for each of the light sensors 170a,b. In the example depicted by FIG. 12 the VAE 115 may calculate average light absorption=[(light absorption 175a1)+(light absorption 175a2)]/2. In FIG. 12, the liquid 185 absorption coefficient a, and the absorbing agent concentration c, are known constants chosen in accordance with the present disclosure, permitting the VAE 115 to calculate light absorption 175a1 and light absorption 175a2 from the received light intensity information received from light sensor 170a and light sensor 175b, respectively. In the example depicted by FIG. 12, the light absorption 175a1 is a function of distance b1 between light emitter 165 and light sensor 170a. In FIG. 12, the light absorption 175a2 is a function of distance b2 between light emitter 165 and light sensor 170b. In the example depicted by FIG. 12, light absorption 175a1 is the product of a, b1 and c, that is, light absorption 175a1=a×b1×c. In the example depicted by FIG. 12, light absorption 175a2 is the product of a, b2 and c, that is, light absorption 175a2=a×b2×c. Using light absorption 175a1 and light absorption 175a2 calculated by VAE 115 from the received light intensity information received by light sensor 170a and light sensor 175b respectively, VAE 115 calculates the distances b1 and b2. VAE 115 calculates the average distance from the distances b1 and b2. VAE 115 uses the average distance to determine the average thickness or distance across the collapsible reservoir 150. In an illustrative example, average light absorption=[(light absorption 175a1)+(light absorption 175a2)]/2=[ac(b1+b2)]/2. Accordingly average distance=total light absorption/ac=[(light absorption 175a1)+(light absorption 175a2)]/ac.

FIG. 13 depicts an exemplary method to make a volume assessment device. In FIG. 13, the exemplary method 1300 begins at step 1305 with selecting an excipient having a light absorption spectrum comprising a magnitude of an absorption coefficient determined for a fixed distance.

The method continues at step 1310 with determining a light wavelength for a light emitter selected to correspond with at least a local maximum light absorption by the excipient, based on the light absorption spectrum.

The method continues at step 1315 with determining a collapsible reservoir maximum length. The collapsible reservoir maximum length may be determined based on designed specifications or requirements for maximum reservoir capacity or device size. The collapsible reservoir maximum length may be less than or equal to a maximum distance through the liquid wherein the excipient concentration results in the linear relationship between distance through the liquid having the excipient concentration and absorption of light by the excipient at the selected wavelength.

The method continues at step 1320 with determining an excipient concentration chosen to result in a linear relationship between distance through a liquid having the excipient concentration and absorption of light by the excipient at the selected wavelength, based on light absorption characteristics of the excipient evaluated as a function of distance. A plurality of light absorption spectra may be determined for a respective plurality of distances and concentrations. The excipient concentration may be chosen as a function of the collapsible reservoir maximum length determined in step 1315.

The method continues at step 1325 with configuring a collapsible reservoir having a variable length separating a collapsible reservoir emitting side from a collapsible reservoir detecting side, wherein the variable length is variable from a collapsible reservoir minimum length to the collapsible reservoir maximum length.

The method continues at step 1330 with selecting a light emitter configured to emit light having the selected light wavelength.

The method continues at step 1335 with selecting a light detector configured to measure received light having the selected light wavelength.

The method continues at step 1340 with determining the amount of light emitted by the light emitter based on measuring an amount of light having the selected light wavelength received through a test medium by the light detector.

The method continues at step 1345 with configuring the collapsible reservoir emitting side with the light emitter disposed to emit light having the selected light wavelength directed to the collapsible reservoir detecting side.

The method continues at step 1350 with configuring the collapsible reservoir detecting side with the light detector disposed to detect light having the selected light wavelength received from the light emitter through a liquid retained by the collapsible reservoir.

The method continues at step 1355 with creating a liquid comprising an active compound formulation having the chosen excipient concentration.

The method continues at step 1360 with loading at least a portion of the collapsible reservoir with the liquid comprising the active compound formulation.

The method continues at step 1365 with activating the light emitter to direct light having the selected wavelength to the light detector through the liquid comprising the active compound formulation retained by the collapsible reservoir.

The method continues at step 1370 with measuring an amount of light absorbed by the liquid comprising the active compound formulation retained by the collapsible reservoir, based on measuring an amount of light received by the light detector through the liquid comprising the active compound formulation and the excipient.

The method continues at step 1375 with calculating a fraction of light absorbed by the liquid comprising the active compound formulation.

The method continues at step 1380 with determining a distance separating the collapsible reservoir emitting side from the collapsible reservoir detecting side as a function of the fraction of light absorbed by the liquid and the linear relationship between distance through the liquid having the excipient concentration and absorption of light by the excipient at the selected wavelength.

The method continues at step 1385 with determining the volume of the collapsible reservoir as a function of the distance separating the collapsible reservoir emitting side from the collapsible reservoir detecting side.

FIG. 14 depicts a process flow of an exemplary volume assessment process. In FIG. 14, the exemplary method 1400 begins at step 1405 with configuring a liquid compromising an active compound formulation with an excipient concentration in the liquid determined to govern a linear relationship between light absorption and distance for a light wavelength preselected as a function of a light absorption spectrum determined for the excipient.

The method continues at step 1410 with loading at least a portion of the collapsible reservoir with the liquid to be retained by the collapsible reservoir.

The method continues at step 1415 with directing light emitted with the predetermined wavelength through the liquid to a light detector disposed in the collapsible reservoir.

The method continues at step 1420 with determining the amount of emitted light absorbed by the liquid, based on measuring the emitted light received by the light detector through the liquid.

The method continues at step 1425 with determining a distance separating the light emitter from the light detector across the collapsible reservoir interior based on the amount of emitted light absorbed by the liquid and the linear relationship between light absorption and distance governed by the excipient concentration in the liquid.

The method continues at step 1430 with determining the volume of the liquid retained by the collapsible reservoir based on the distance separating the light emitter from the light detector.

Although various features have been described with reference to the Figures, other features are possible. For example, disclosed herein are exemplary implementations of novel therapeutic fluid formulations. The therapeutic fluid formulation may comprise a medication. The medication may be retained by a reservoir. The reservoir may provide a supply of the medication to an implantable device. The implanted device may be implanted in a patient to administer the formulation of medication to the patient from the reservoir. In the case of implanted pumps with intrathecal catheters, the medication may be, for example, baclofen or morphine. Such an exemplary medication formulation may be modified with the addition of an excipient such as methylene blue or fluorescein. The combination of active compound and excipient achieves the technical advantage of real-time spectrometric assessment of reservoir volume as disclosed herein. Some implementations may decrease the adverse effects and risks from mismatch between expected and actual reservoir volume. Such decreased adverse effects and risks from mismatch between expected and actual reservoir volume may be a result of the medication formulation comprising an active compound with an excipient in a concentration governing a linear relationship between distance and light absorption at the preselected wavelength, disclosed herein.

Various techniques that would be known to one of ordinary skill may be employed to construct and calibrate an exemplary intrathecal pump device or perform an exemplary volume assessment method in accordance with the teaching of the present disclosure. For example, in quantitative absorption spectrometry, the absorption of light having a preselected wavelength through a liquid, with zero concentration of species, or in this case, excipient, may be obtained. Then this number is subtracted from subsequent absorption measurements with some concentration(s) of excipient greater than zero—this assumes that after adding excipient, the concentrations of agents in the original liquid (and therefore their additions to gross absorption) does not change as a result of adding the excipient. Then concentration can be calculated using the net calculated absorption and the known molar extinction coefficient. This last step may only be needed when initially determining the appropriate concentration of excipient to formulate in order to achieve a linear relationship between reservoir length and absorption. Calibration to air or free space need never factor in.

In an illustrative example, the maximum reservoir length may govern the excipient concentration and selected light wavelength. Once maximum reservoir length is established as part of the design specs, the process summarized above may be used to determine appropriate concentration of excipient. At this maximum length, the liquid (for example morphine or baclofen in some electrolyte solution without added excipient) absorption at selected wavelength may already approach close to one. Any subsequently added excipient would likely saturate the absorption signal (non-linear response). However, this is unlikely in the context of the present disclosure because wavelengths in the visible spectrum are being considered here and some medication formulations may be indistinguishable from water, resulting in formulations that are substantially translucent to visible light (low molar absorption coefficient at selected wavelength).

Once the appropriate concentration of excipient is selected for reservoir size constraints, the formulation concentration remains constant in the reservoir. A significant advantage of the disclosed techniques is that once the reservoir is filled to maximum and absorption at the 'maximum' length is measured (this can be every time the reservoir is filled), subsequent measurements and calculations of volume during emptying of the reservoir can be relative to the full state.

For example:

{Full reservoir,maximum length}==>A=0.8

{Half filled,half maximum length}==>A=0.4

{Empty,zero length}==>A=0

An exemplary volume assessment implementation may be designed to employ one or more techniques to perform light absorption and distance measurements that would be available to one of ordinary skill in the art.

In one example, a volume assessment implementation in accordance with the present disclosure may perform light absorption and distance measurements by measuring the light received by all the detectors for each individual emitter through the liquid for each individual emitter and store the light intensity measured by the detector receiving the greatest light. When all the individual emitters are processed this way there will be a group of multiple maximum light intensities, and they may be summed and averaged to obtain the average light received through the liquid by the multiple detectors. This would be compared with a similar measurement made through a test medium in the reservoir to determine the average light absorbed and then distance.

In another example, a volume assessment implementation in accordance with the present disclosure may perform light absorption and distance measurements by measuring the light received for each individual emitter by all the detectors through the liquid for each individual emitter, store the light intensity measured by the detector receiving the greatest light and store the light intensities measured by the other detectors that were receiving less light. When all the individual emitters are processed this way there will be a group of multiple maximum light intensities (one from each group) and multiple groups of lesser light intensities (one group of lesser intensities for each set of detectors). For each set of detectors subtracting the average of the lesser intensities from the maximum intensity and summing and averaging their difference intensities would obtain the average light received through the liquid by the multiple detectors. This would be compared with a similar measurement made through a test medium in the reservoir to determine the average light absorbed and then distance. This method may improve accuracy because the dispersion from each emitter to each detector could be canceled out.

In another example, a volume assessment implementation in accordance with the present disclosure may perform light absorption and distance measurements based on determining the locations of all the emitters and detectors relative to each other and using geometric relationships (for example, the Pythagorean theorem) and the linear relationship between distance through the liquid and absorption (governed by a predetermined excipient concentration and preselected wavelength) to determine the fraction of the light absorbed. This method may place more rigorous constraints on the reservoir and locations of the emitters and detectors.

A volume assessment implementation in accordance with the teaching of the present disclosure may have a concentration of dye such that the absorption across all volumes of the reservoir will be between $0<$absorption$<1$ and preferably $0.2<$absorption$<0.8$. At absorptions approaching 1, the signal will be saturation and a linear relationship between dye concentration and absorption will no longer exist.

A volume assessment implementation in accordance with the teaching of the present disclosure may comprise for example, one or more of an LED diode, a Photo-resistor, wires from diode and resistor to a pump electronics unit, a modified PCB to handle input/outputs to diode and resistor, electronic firmware, a reservoir solution with excipient in the form of a dye with maximum absorptivity coefficient matched to LED diode frequency/wavelength of emitted light, and a linear relationship between dye concentration and absorption.

Description of the Beer-Lambert Law Aka Beer's Law

The Beer-Lambert (Beer's) law is used in many clinical devices and settings that include the Oxygen Hemoglobin Pulse oximeter, ABG machines that implement Co-Oximetry, and infrared spectroscopic gas ($CO_2$, $N_2O$, volatile agent) analysis. Beer's law states that $A=abc$, where A is absorption of some wavelength of light through some chemical agent, c is the concentration of same chemical agent, a is the absorptivity constant for same chemical agent at some wavelength of light, and b is the distance between a light emitter (e.g., a diode) and a light detector (e.g., photo resistor).

Typically, Beer's law is used to measure the concentration of some chemical agent, and a and b are held constant. For example, as $CO_2$ sampled from a patient flows between a light emitter and light detector with fixed distance b between them, A is measured using absorption spectroscopy and c is calculated using a rearrangement of Beer's law, $c=A/(ab)$. The Pulse oximeter uses Beer's law in more complex ways to measure the O2 saturation of hemoglobin in arterial blood. A co-oximeter uses Beer's law to measure the proportions of several species of hemoglobin (Oxy-Hb, carboxy-Hb, Met-Hg) in a sample of blood.

Application of Beer's Law Relevant to the Teaching of the Present Disclosure

An application of Beer's law applied by the teaching of the present disclosure is reflected in the rearrangement, $b=A/(ac)$, where a and c are held constant. This relationship is implemented using a reservoir whose volume is variable and which depends on reservoir length. The general shape of the reservoir will be assumed to be of a cylindrical accordion type as this shape may be exemplary of currently implemented devices, however the volume of any reservoir geometry may be determined by one of ordinary skill using the techniques disclosed herein.

In an illustrative example, a photo LED diode that emits light at a certain wavelength (say 660 nm, red) is at one end of the accordion, and a photo resistor sensitive to the wavelength is on the other side and is capable of measuring the amplitude (intensity) of light that reaches it. The reservoir is filled with liquid containing a specified concentration of dye capable of absorbing light emitted by the diode. In this case, a dye like methylene blue is appropriate because it absorbs red light-its absorptivity coefficient, a, at 660 nm is relatively large. An implementation in accordance with the present disclosure may use fluorescein or any other absorbing agent that obeys Beer's law as an excipient.

Methylene blue is also appropriate because methylene blue already has a role in many clinical settings and is administered to patients. Additionally, only a small molar amount of methylene blue is needed for absorption to be linear over the range relevant to the current invention. As such, by measuring the absorption between diode and resistor at any time, distance b can be accurately calculated and by extension the reservoir volume.

An implementation in accordance with the present disclosure may achieve one or more advantageous technical effects. In illustrative scenarios exemplary of prior art volume assessment designs, an implementation in accordance with the present disclosure may advantageously provide more accurate reservoir volume measurements. For example, some prior art volume assessment systems employ less accurate predictive techniques. In an illustrative example a volume assessment system employing predictive techniques in an implanted device may use device electronics to track the dynamic flow rate from a peristaltic pump over time and integrate the area under the flowrate versus time curve. Unfortunately, the actual flow rate may differ from device to device and over time for the same device, relative to engineered specifications for such prior art systems employing predictive volume assessment techniques. Over the volume cycle of a reservoir, predicted remaining reservoir volume may be significantly different than actual volume. The 'real-time' assessment in accordance with the present disclosure is, therefore, an improvement over the current art.

An exemplary method may comprise: directing emitted light (167) with a predetermined light wavelength (610) from a light emitter (165) through a volume of a liquid (185) retained by a collapsible reservoir (150), wherein the liquid comprises an active compound formulation (145) with an excipient (155) present in an excipient concentration (160) determined to result in a linear relationship between light absorption (175) and distance (180) for the predetermined light wavelength (610), using a computer processor (200) and the light emitter (165); receiving at least a portion of light emitted (167) by the light emitter (165) through the liquid (185), using a light sensor (170) disposed in the collapsible reservoir (150); determining an amount of emitted light (167) absorbed by the liquid (185), based on measuring the amount of the emitted light (167) from the light emitter (165) that is received by the light sensor (170), using the computer processor (200) and the light sensor (170); and determining a distance (180) separating the light emitter (165) from the light sensor (170) across the collapsible reservoir (150) interior based on the amount of emitted light (167) absorbed by the liquid (185) and the linear relationship between light absorption (175) and distance (180) for the predetermined light wavelength (610), using the computer processor (200).

The method may further comprise determining the excipient concentration (160) resulting in the linear relationship between light absorption (175) and distance (180) for the predetermined light wavelength (610).

The method may further comprise selecting the predetermined light wavelength (610) based on a predetermined excipient concentration (160).

The method may further comprise configuring the liquid (185) comprising the active compound formulation (145) with the excipient concentration (160) determined to result in the linear relationship between light absorption (175) and distance (180) for the predetermined light wavelength (610).

The method may further comprise loading at least a portion of the collapsible reservoir (150) with the liquid (185).

The collapsible reservoir (150) may be retained by a cavity (245).

The cavity (245) may be pressurized to a cavity interior pressure greater than collapsible reservoir (150) interior pressure.

The method may further comprise determining the volume of the liquid (185) retained by the collapsible reservoir (150) based on the distance (180) separating the light emitter (165) from the light sensor (170), using the computer processor (200).

The method may further comprise storing data representing the volume of the liquid (185) retained by the collapsible reservoir (150) in a computer memory (205), using the computer processor (200).

The method may further comprise sending an electronic message reporting the volume of the liquid (185), wherein the electronic message comprises data representing the volume of the liquid (185) retained by the collapsible reservoir (150), using the computer processor (200).

The method may further comprise determining if the volume of the liquid (185) retained by the collapsible reservoir (150) is greater than a predetermined maximum threshold volume, using the computer processor (200).

The method may further comprise: in response to determining the volume of the liquid (185) retained by the collapsible reservoir (150) is greater than the predetermined maximum threshold volume, refraining from sending an electronic message reporting the volume of the liquid (185), using the computer processor (200).

The method may further comprise: in response to determining the volume of the liquid (185) retained by the collapsible reservoir (150) is not greater than the predetermined maximum threshold volume, sending an electronic message reporting the volume of the liquid (185), using the computer processor (200).

The excipient (155) may comprise methylene blue.

The excipient (155) may comprise fluorescein.

The active compound formulation (145) may comprise morphine.

The active compound formulation (145) may comprise baclofen.

An exemplary method may comprise: configuring a light emitter (165) to direct emitted light (167) with a predetermined light wavelength (610) through a liquid (185) retained by a collapsible reservoir (150) to a light sensor (170) disposed in the collapsible reservoir (150), wherein the liquid (185) comprises an active compound formulation (145) with an excipient (155) present in an excipient concentration (160) governing a linear relationship between light absorption (175) by the liquid (185) at a preselected light wavelength (610) and distance (180) through the liquid (185), using a computer processor (200) and the light emitter (165); and determining a distance (180) separating the light emitter (165) from the light sensor (170) across the collapsible reservoir (150) interior based on an amount of emitted light (167) absorbed by the liquid (185), using the computer processor (200) and the light sensor (170).

The method may further comprise determining a volume of the liquid (185) retained by the collapsible reservoir (150), wherein the volume of the liquid (185) retained by the collapsible reservoir is determined as a function of the distance (180) separating the light emitter (165) from the light sensor (170), using the computer processor (200).

The excipient (155) may comprise methylene blue.

The active compound formulation (145) may comprise morphine.

The method may further comprise determining the distance (180) across the collapsible reservoir (150) as a function of the linear relationship between light absorption (175) by the liquid (185) at the preselected light wavelength (610) and distance (180) through the liquid (185), using the computer processor (200).

The method may further comprise providing real-time measurements of remaining liquid (185) volume as the liquid (185) is depleted and the collapsible reservoir (150) collapses, using the computer processor (200).

An exemplary method may comprise: activating one light emitter (165) to transmit emitted light (167) with a predetermined light wavelength (610) through a liquid (185) retained by a collapsible reservoir (150) to two or more light sensors (170) disposed in the collapsible reservoir (150), using a computer processor (200) and the one light emitter (165); determining an average distance (180) across the collapsible reservoir (150) interior based on an amount of emitted light (167) absorbed by the liquid (185) determined as a function of an average amount of the emitted light (167) received by the two or more light sensors (170), using the computer processor (200) and the two or more light sensors (170); and determining a volume of the liquid (185) retained by the collapsible reservoir (150) as a function of the average distance (180) across the collapsible reservoir (150) interior.

The liquid (185) may comprise an active compound formulation (145) with an excipient (155) present in an excipient concentration (160) governing a linear relationship between light absorption (175) by the liquid (185) at a preselected wavelength (610) and distance (180) through the liquid (185).

The liquid (185) may comprise morphine and methylene blue.

The liquid (185) may comprise baclofen and methylene blue.

The liquid (185) may comprise morphine and fluorescein.

The liquid (185) may comprise baclofen and fluorescein.

The method may further comprise: determining if the volume of the liquid (185) retained by the collapsible reservoir (150) is greater than a predetermined maximum threshold volume; and in response to determining the volume of the liquid (185) retained by the collapsible reservoir (150) is not greater than the predetermined maximum threshold volume, sending an electronic message reporting the volume of the liquid (185), using the computer processor (200).

An exemplary method may comprise: cycling each light emitter (165) of at least two light emitters (165) through a respective on and off sequence comprising a light emitting time period and a dark time period to cause each light emitter (165) of the at least two light emitters (165) to transmit emitted light (167) from one light emitter (165) of the at least two light emitters (165) at a time through a liquid (185) retained by a collapsible reservoir (150) to at least two light sensors (170) disposed in the collapsible reservoir (150), using a computer processor (200) and the at least two light emitters (165); determining a sum amount of emitted light (167) received by the at least two light sensors (170) from the at least two light emitters (165) based on adding an amount of emitted light (167) received by the at least two light sensors (170) during at least two light emitting time periods, using the computer processor (200) and the at least two light sensors (170); determining an average amount of the emitted light (167) received by each light sensor (170) of the at least two light sensors (170) during at least two light emitting time periods, using the computer processor (200); and determining an average distance (180) across the collapsible reservoir (150) interior based on the average amount of emitted light (167) absorbed by the liquid (185) determined as a function of the average amount of the emitted light (167) received by each light sensor (170) of the at least two light sensors (170) during the at least two light emitting time periods, using the computer processor (200).

Determining an average amount of the emitted light (167) received by each light sensor (170) of the at least two light sensors (170) during at least two light emitting time periods may further comprise dividing the sum amount of emitted light (167) received by the at least two light sensors (170) from the at least two light emitters (165) by an arithmetic product comprising of a count of the at least two light sensors (170) multiplied by a count of the at least two light emitting time periods, using the computer processor (200).

The method may further comprise determining a volume of the liquid (185) retained by the collapsible reservoir (150) as a function of the average distance (180) across the collapsible reservoir (150) interior, using the computer processor (200).

The method may further comprise determining the sum amount of emitted light (167) received by the at least two light sensors (170) individually from each light emitter (165) of the at least two light emitters (165), based on determining the sum amount of emitted light (167) received by each of the at least two light sensors (170) that received more emitted light (167) during successive on time periods, using the at least two light emitters (165), the at least two light sensors (170) and the computer processor (200).

The method may further comprise determining the sum amount of emitted light (167) received by the at least two light sensors (170) individually from each light emitter (165) of the at least two light emitters (165) based on subtracting an amount of emitted light (167) received by each of the at least two light sensors (170) that received less emitted light (167) from the amount of emitted light (167) received by each of the at least two light sensors (170) that received more emitted light (167) during successive on time periods, using the at least two light emitters (165), the at least two light sensors (170) and the computer processor (200).

In the Summary above, in this Detailed Description, the Claims below, the content of each of the applications incorporated by reference herein and in the accompanying drawings, reference is made to features of various embodiments of the invention. It is to be understood that the disclosure of embodiments of the invention in this specification includes all possible combinations of such features. For example, where a particular feature is disclosed in the context of a particular aspect or embodiment of the invention, or a particular claim, that feature can also be used—to the extent possible—in combination with and/or in the context of other aspects and embodiments of the invention, and in the invention generally.

The present disclosure teaches implanted reservoir volume assessment. Implanted reservoir volume assessment may be implemented as a method. Implanted reservoir volume assessment may be implemented as an apparatus. The apparatus may be configured to implement operations of the method. An exemplary implanted reservoir volume assessment method may implement operations that when performed result in one or more technical effects the same as or substantially similar to technical effects that may result from operating an exemplary volume assessment apparatus. Implanted reservoir volume assessment may be implemented as a computer readable storage medium. The computer readable storage medium may comprise processor executable program instructions configured to cause at least a portion of an apparatus to perform an exemplary implanted reservoir volume assessment method. The computer readable storage medium may comprise processor executable program instructions configured to cause an apparatus to implement exemplary implanted reservoir volume assessment operations.

While multiple implementations are disclosed, still other implementations will become apparent to those skilled in the art from this detailed description. Disclosed implementations may be capable of myriad modifications, all without departing from the spirit and scope of the disclosed implementations. Accordingly, the drawings and descriptions are to be regarded as illustrative in nature and not restrictive.

It should be noted that the features illustrated in the drawings are not necessarily drawn to scale, and features of one implementation may be employed with other implementations as the skilled artisan would recognize, even if not explicitly stated herein. Descriptions of well-known components and processing techniques may be omitted so as to not unnecessarily obscure the implementation features.

In the present disclosure, various features may be described as being optional, for example, through the use of the verb "may;" or, through the use of any of the phrases: "in some implementations," "in some designs," "in various implementations," "in various designs," "in an illustrative example," or, "for example." For the sake of brevity and legibility, the present disclosure does not explicitly recite each and every permutation that may be obtained by choosing from the set of optional features. However, the present disclosure is to be interpreted as explicitly disclosing all such permutations. For example, a system described as having three optional features may be implemented in seven different ways, namely with just one of the three possible features, with any two of the three possible features or with all three of the three possible features.

In various implementations, elements described herein as coupled or connected may have an effectual relationship realizable by a direct connection or indirectly with one or more other intervening elements.

In the present disclosure, the term "any" may be understood as designating any number of the respective elements, that is, as designating one, at least one, at least two, each or all of the respective elements. Similarly, the term "any" may be understood as designating any collection(s) of the respective elements, that is, as designating one or more collections of the respective elements, a collection comprising one, at least one, at least two, each or all of the respective elements. The respective collections need not comprise the same number of elements.

While various implementations have been disclosed and described in detail herein, it will be apparent to those skilled in the art that various changes may be made to the disclosed configuration, operation, and form without departing from the spirit and scope thereof. It is noted that the respective implementation features, even those disclosed solely in combination with other implementation features, may be combined in any configuration excepting those readily apparent to the person skilled in the art as nonsensical. Likewise, use of the singular and plural is solely for the sake of illustration and is not to be interpreted as limiting.

Certain terminology and derivations thereof may be used in the present disclosure for convenience in reference only and will not be limiting. For example, words such as "upward," "downward," "left," and "right" would refer to directions in the drawings to which reference is made unless otherwise stated. Similarly, words such as "inward" and "outward" would refer to directions toward and away from, respectively, the geometric center of a device or area and designated parts thereof. References in the singular tense include the plural, and vice versa, unless clear from the context or otherwise noted.

The term "comprises" and grammatical equivalents thereof are used herein to mean that other components, ingredients, steps, among others, are optionally present. For example, an implementation "comprising" (or "which comprises") components A, B and C can consist of (that is, contain only) components A, B and C, or can contain not only components A, B, and C but also contain one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example, "at least 1" means 1 or more than 1. The term "at most" followed by a number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)–(a second number)," this means a range whose limit is the second number. For example, 25 to 100 mm means a range whose lower limit is 25 mm and upper limit is 100 mm.

Many suitable methods and corresponding materials to make each of the individual parts of implementation apparatus are known in the art. One or more implementation part may be formed by machining, 3D printing (also known as "additive" manufacturing), CNC machined parts (also known as "subtractive" manufacturing), and injection molding, as will be apparent to a person of ordinary skill in the art. Metals, wood, thermoplastic and thermosetting polymers, resins and elastomers as may be described hereinabove may be used. Many suitable materials are known and available and can be selected and mixed depending on desired strength and flexibility, preferred manufacturing method and particular use, as will be apparent to a person of ordinary skill in the art.

Any element in a claim herein that does not explicitly state "means for" performing a specified function, or "step for" performing a specific function, is not to be interpreted as a "means" or "step" clause as specified in 35 U.S.C. § 112 (f). Specifically, any use of "step of" in the claims herein is not intended to invoke the provisions of 35 U.S.C. § 112 (f). Elements recited in means-plus-function format are intended to be construed in accordance with 35 U.S.C. § 112 (f).

Recitation in a claim of the term "first" with respect to a feature or element does not necessarily imply the existence of a second or additional such feature or element.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The terms "abutting" or "in mechanical union" refer to items that are in direct physical contact with each other, although the items may not necessarily be attached together.

The word "exemplary" is used herein to mean "serving as an example, instance, or illustration." Any implementation described herein as "exemplary" is not necessarily to be construed as preferred over other implementations. While various aspects of the disclosure are presented with reference to drawings, the drawings are not necessarily drawn to scale unless specifically indicated.

Reference throughout this specification to "an implementation" or "the implementation" means that a particular feature, structure, or characteristic described in connection with that implementation is included in at least one implementation. Thus, the quoted phrases, or variations thereof, as recited throughout this specification are not necessarily all referring to the same implementation.

Similarly, it should be appreciated that in the above description, various features are sometimes grouped together in a single implementation, Figure, or description thereof for the purpose of streamlining the disclosure. This method of disclosure, however, is not to be interpreted as reflecting an intention that any claim in this or any application claiming priority to this application require more features than those expressly recited in that claim. Rather, as the following claims reflect, inventive aspects may lie in a combination of fewer than all features of any single foregoing disclosed implementation. Thus, the claims following this Detailed Description are hereby expressly incorporated into this Detailed Description, with each claim standing on its own as a separate implementation. This disclosure is intended to be interpreted as including all permutations of the independent claims with their dependent claims.

A system or method implementation in accordance with the present disclosure may be accomplished through the use of one or more computing devices. As depicted, for example, at least in FIG. 1 and FIG. 2, one of ordinary skill in the art would appreciate that an exemplary system appropriate for use with implementation in accordance with the present application may generally include one or more of a Central processing Unit (CPU), Random Access Memory (RAM), a storage medium (e.g., hard disk drive, solid state drive, flash memory, cloud storage), an operating system (OS), one or more application software, a display element, one or more communications means, or one or more input/output devices/means. Examples of computing devices usable with implementations of the present disclosure include, but are not limited to, proprietary computing devices, personal computers, mobile computing devices, tablet PCs, mini-PCs, servers, or any combination thereof. The term computing device may also describe two or more computing devices communicatively linked in a manner as to distribute and share one or more resources, such as clustered computing devices and server banks/farms. One of ordinary skill in the art would understand that any number of computing devices could be used, and implementations of the present disclosure are contemplated for use with any computing device.

In various implementations, communications means, data store(s), processor(s), or memory may interact with other components on the computing device, in order to effect the provisioning and display of various functionalities associated with the system and method detailed herein. One of ordinary skill in the art would appreciate that there are numerous configurations that could be utilized with implementations of the present disclosure, and implementations of the present disclosure are contemplated for use with any appropriate configuration.

According to an implementation of the present disclosure, a communications means of the system may be, for instance, any means for communicating data over one or more networks or to one or more peripheral devices attached to the system. Appropriate communications means may include, but are not limited to, circuitry and control systems for providing wireless connections, wired connections, cellular connections, data port connections, Bluetooth® connections, or any combination thereof. One of ordinary skill in the art would appreciate that there are numerous communications means that may be utilized with implementations of the present disclosure, and implementations of the present disclosure are contemplated for use with any communications means.

Throughout this disclosure and elsewhere, block diagrams and flowchart illustrations depict methods, apparatuses (i.e., systems), and computer program products. Each element of the block diagrams and flowchart illustrations, as well as each respective combination of elements in the block diagrams and flowchart illustrations, illustrates a function of the methods, apparatuses, and computer program products. Any and all such functions ("depicted functions") can be implemented by computer program instructions; by special-purpose, hardware-based computer systems; by combinations of special purpose hardware and computer instructions; by combinations of general-purpose hardware and computer instructions; and so on—any and all of which may be generally referred to herein as a "circuit," "module," or "system."

While the foregoing drawings and description may set forth functional aspects of the disclosed systems, no particular arrangement of software for implementing these functional aspects should be inferred from these descriptions unless explicitly stated or otherwise clear from the context.

Each element in flowchart illustrations may depict a step, or group of steps, of a computer-implemented method. Further, each step may contain one or more sub-steps. For the purpose of illustration, these steps (as well as any and all other steps identified and described above) are presented in order. It will be understood that an implementation may include an alternate order of the steps adapted to a particular application of a technique disclosed herein. All such variations and modifications are intended to fall within the scope of this disclosure. The depiction and description of steps in any particular order is not intended to exclude implementations having the steps in a different order, unless required by a particular application, explicitly stated, or otherwise clear from the context.

Traditionally, a computer program consists of a sequence of computational instructions or program instructions. It will be appreciated that a programmable apparatus (that is, computing device) can receive such a computer program and, by processing the computational instructions thereof, produce a further technical effect.

A programmable apparatus may include one or more microprocessors, microcontrollers, embedded microcontrollers, programmable digital signal processors, programmable devices, programmable gate arrays, programmable array logic, memory devices, application specific integrated circuits, or the like, which can be suitably employed or configured to process computer program instructions, execute computer logic, store computer data, and so on. Throughout this disclosure and elsewhere a computer can include any and all suitable combinations of at least one general purpose computer, special-purpose computer, programmable data processing apparatus, processor, processor architecture, and so on.

It will be understood that a computer can include a computer-readable storage medium and that this medium may be internal or external, removable, and replaceable, or fixed. It will also be understood that a computer can include a Basic Input/Output System (BIOS), firmware, an operating system, a database, or the like that can include, interface with, or support the software and hardware described herein.

Implementations of the system as described herein are not limited to applications involving conventional computer programs or programmable apparatuses that run them. It is contemplated, for example, that implementations of the disclosure as claimed herein could include an optical computer, quantum computer, analog computer, or the like.

Regardless of the type of computer program or computer involved, a computer program can be loaded onto a computer to produce a particular machine that can perform any and all of the depicted functions. This particular machine provides a means for carrying out any and all of the depicted functions.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be a computer readable storage medium or memory that is not a transitory propagating signal. A computer readable storage medium may be any tangible medium that can contain or store a program for use by or in connection with an instruction execution system, apparatus, or device.

Computer program instructions can be stored in a computer-readable memory capable of directing a computer or other programmable data processing apparatus to function in a particular manner. The instructions stored in the computer-readable memory constitute an article of manufacture including computer-readable instructions for implementing any and all of the depicted functions.

A computer readable signal medium may include a propagated data signal with computer readable program code encoded therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code encoded by a computer readable medium may be transmitted using any appropriate medium, including but not limited to wireless, wireline, optical fiber cable, RF, etc., or any suitable combination of the foregoing.

The elements depicted in flowchart illustrations and block diagrams throughout the figures imply logical boundaries between the elements. However, according to software or hardware engineering practices, the depicted elements and the functions thereof may be implemented as parts of a monolithic software structure, as standalone software modules, or as modules that employ external routines, code, services, and so forth, or any combination of these. All such implementations are within the scope of the present disclosure.

Unless explicitly stated or otherwise clear from the context, the verbs "execute" and "process" are used interchangeably to indicate execute, process, interpret, compile, assemble, link, load, any and all combinations of the foregoing, or the like. Therefore, implementations that execute or process computer program instructions, computer-executable code, or the like can suitably act upon the instructions or code in any and all of the ways just described.

The functions and operations presented herein are not inherently related to any particular computer or other apparatus. Various general-purpose systems may also be used with programs in accordance with the teachings herein, or it may prove convenient to construct more specialized apparatus to perform the required method steps. The required structure for a variety of these systems will be apparent to those of skill in the art, along with equivalent variations. In addition, implementations of the disclosure are not described with reference to any particular programming language. It is appreciated that a variety of programming languages may be used to implement the present teachings as described herein, and any references to specific languages are provided for disclosure of enablement and best mode of implementations of the disclosure. Implementations of the disclosure are well suited to a wide variety of computer network systems over numerous topologies. Within this field, the configuration and management of large networks include storage devices and computers that are communicatively coupled to dissimilar computers and storage devices over a network, such as the Internet.

The names and reference numbers of elements depicted by the Drawings are summarized as follows:
scenario 100
doctor 105
intrathecal pump device 110
volumetric assessment engine (VAE) 115
patient 120
mobile device 125
server 130
network cloud 135
pump 140
active compound formulation 145
reservoir 150
excipient 155
excipient concentration 160
light emitter 165
emitted light 167
light sensor 170
light absorption 175
distance 180
liquid 185
computer processor 200
computer memory 205
input/output (I/O) interface 210
communication interface 215
battery 220
side catheter access port 225
catheter port 230
reservoir port 235
antenna 240
cavity 245
program memory 400
data memory 405
storage medium 410
user interface 415
sensor interface 420
emitter interface 425
pump interface 430
excipient light absorption response 500
absorption A 505
distance 510
linear region 515
non-linear region 520
excipient light absorption spectrum 600
excipient molar light absorption coefficient 605
light wavelength 610
local maximum 615
global maximum 620
volume assessment device construction process 1300
volume assessment process 1400

The present disclosure intends that the invention is not limited to any embodiment disclosed herein as an example of making or using the invention, but that the invention will be considered to include all embodiments falling within the scope of the present disclosure as set forth in the following claims. These following claims should be construed to maintain the proper protection for the present invention.

What is claimed is:
1. A method comprising:
directing emitted light with a predetermined light wavelength from a light emitter through a volume of a liquid retained by a collapsible reservoir, wherein the liquid comprises an active compound formulation with an excipient present in an excipient concentration determined to result in a linear relationship between light absorption and distance for the predetermined light wavelength, using a computer processor and the light emitter;

receiving at least a portion of light emitted by the light emitter through the liquid, using a light sensor disposed in the collapsible reservoir;

determining an amount of emitted light absorbed by the liquid, based on measuring the amount of the emitted light from the light emitter that is received by the light sensor, using the computer processor and the light sensor; and determining a distance separating the light emitter from the light sensor across the collapsible reservoir interior based on the amount of emitted light absorbed by the liquid and the linear relationship between light absorption and distance for the predetermined light wavelength, using the computer processor.

2. The method of claim 1, wherein the method further comprises determining the excipient concentration resulting in the linear relationship between light absorption and distance for the predetermined light wavelength.

3. The method of claim 1, wherein the method further comprises selecting the predetermined light wavelength based on a predetermined excipient concentration.

4. The method of claim 1, wherein the method further comprises configuring the liquid comprising the active compound formulation with the excipient concentration determined to result in the linear relationship between light absorption and distance for the predetermined light wavelength.

5. The method of claim 1, wherein the method further comprises loading at least a portion of the collapsible reservoir with the liquid.

6. The method of claim 1, wherein the collapsible reservoir is retained by a cavity.

7. The method of claim 6, wherein the cavity is pressurized to a cavity interior pressure greater than collapsible reservoir interior pressure.

8. The method of claim 1, wherein the method further comprises determining the volume of the liquid retained by the collapsible reservoir based on the distance separating the light emitter from the light sensor, using the computer processor.

9. The method of claim 8, wherein the method further comprises storing data representing the volume of the liquid retained by the collapsible reservoir, wherein the data is stored in a computer memory, using the computer processor.

10. The method of claim 8, wherein the method further comprises sending an electronic message reporting the volume of the liquid, wherein the electronic message comprises data representing the volume of the liquid retained by the collapsible reservoir, using the computer processor.

11. The method of claim 8, wherein the method further comprises determining if the volume of the liquid retained by the collapsible reservoir is greater than a predetermined threshold volume, using the computer processor.

12. The method of claim 11, wherein in response to determining the volume of the liquid retained by the collapsible reservoir is greater than the predetermined threshold volume, the method further comprises refraining from sending an electronic message reporting the volume of the liquid, using the computer processor.

13. The method of claim 11, wherein in response to determining the volume of the liquid retained by the collapsible reservoir is not greater than the predetermined threshold volume, the method further comprises sending an electronic message reporting the volume of the liquid, using the computer processor.

14. The method of claim 1, wherein the excipient comprises methylene blue.

15. The method of claim 1, wherein the excipient comprises fluorescein.

16. The method of claim 1, wherein the active compound formulation comprises morphine.

17. The method of claim 1, wherein the active compound formulation comprises baclofen.

18. A method comprising:

configuring a light emitter to direct emitted light with a predetermined light wavelength through a liquid retained by a collapsible reservoir to a light sensor disposed in the collapsible reservoir, wherein the liquid comprises an active compound formulation with an excipient present in an excipient concentration governing a linear relationship between light absorption by the liquid at a preselected light wavelength and distance through the liquid, using a computer processor and the light emitter; and determining a distance separating the light emitter from the light sensor across the collapsible reservoir interior based on an amount of emitted light absorbed by the liquid, using the computer processor and the light sensor.

19. The method of claim 18, wherein the method further comprises determining a volume of the liquid retained by the collapsible reservoir, wherein the volume of the liquid retained by the collapsible reservoir is determined as a function of the distance separating the light emitter from the light sensor, using the computer processor.

20. The method of claim 18, wherein the excipient further comprises methylene blue.

21. The method of claim 18, wherein the active compound formulation further comprises morphine.

22. The method of claim 18, wherein the method further comprises determining the distance across the collapsible reservoir as a function of the linear relationship between light absorption by the liquid at the preselected light wavelength and distance through the liquid, using the computer processor.

23. The method of claim 18, wherein the method further comprises providing real-time measurements of remaining liquid volume as the liquid is depleted and the collapsible reservoir collapses, using the computer processor.

24. A method comprising:

activating one light emitter to transmit emitted light with a predetermined light wavelength through a liquid retained by a collapsible reservoir to two or more light sensors disposed in the collapsible reservoir, using a computer processor and the one light emitter;

determining an average distance across the collapsible reservoir interior based on an amount of emitted light absorbed by the liquid determined as a function of an average amount of the emitted light received by the two or more light sensors, using the computer processor and the two or more light sensors; and determining a volume of the liquid retained by the collapsible reservoir as a function of the average distance across the collapsible reservoir interior.

25. The method of claim 24, wherein the liquid comprises an active compound formulation with an excipient present in an excipient concentration governing a linear relationship between light absorption by the liquid at a preselected wavelength and distance through the liquid.

26. The method of claim 24, wherein the liquid further comprises morphine and methylene blue.

27. The method of claim 24, wherein the method further comprises:
- determining if the volume of the liquid retained by the collapsible reservoir is greater than a predetermined threshold volume; and
- in response to determining the volume of the liquid retained by the collapsible reservoir is not greater than the predetermined threshold volume, sending an electronic message reporting the volume of the liquid, using the computer processor (200).

28. A method comprising:
- cycling each light emitter of at least two light emitters through a respective on and off sequence comprising a light emitting time period and a dark time period to cause each light emitter of the at least two light emitters to transmit emitted light from one light emitter of the at least two light emitters at a time through a liquid retained by a collapsible reservoir to at least two light sensors disposed in the collapsible reservoir, using a computer processor and the at least two light emitters;
- determining a sum amount of emitted light received by the at least two light sensors from the at least two light emitters based on adding an amount of emitted light received by the at least two light sensors during at least two light emitting time periods, using the computer processor and the at least two light sensors;
- determining an average amount of the emitted light received by each light sensor of the at least two light sensors during the at least two light emitting time periods, using the computer processor; and
- determining an average distance across the collapsible reservoir interior based on the average amount of emitted light absorbed by the liquid determined as a function of the average amount of the emitted light received by each light sensor of the at least two light sensors during the at least two light emitting time periods, using the computer processor.

29. The method of claim 28, wherein determining an average amount of the emitted light received by each light sensor of the at least two light sensors during the at least two light emitting time periods further comprises dividing the sum amount of emitted light received by the at least two light sensors from the at least two light emitters by an arithmetic product comprising a count of the at least two light sensors multiplied by a count of the at least two light emitting time periods, using the computer processor.

30. The method of claim 28, wherein the method further comprises determining a volume of the liquid retained by the collapsible reservoir as a function of the average distance across the collapsible reservoir interior, using the computer processor.

\* \* \* \* \*

UNITED STATES PATENT AND TRADEMARK OFFICE
CERTIFICATE OF CORRECTION

| | | |
|---|---|---|
| PATENT NO. | : 12,140,463 B1 | Page 1 of 1 |
| APPLICATION NO. | : 18/542264 | |
| DATED | : November 12, 2024 | |
| INVENTOR(S) | : Richard McNeer | |

It is certified that error appears in the above-identified patent and that said Letters Patent is hereby corrected as shown below:

On the Title Page

Item (54) and in the Specification Column 1, Lines 1-2, Title: replace "METHOD INCLUDING OPTICAL DETECTION" with -- IMPLANTED RESERVOIR VOLUME ASSESSMENT METHOD INCLUDING OPTICAL DETECTION -- therefore.

Signed and Sealed this
Fourteenth Day of January, 2025

Derrick Brent
*Acting Director of the United States Patent and Trademark Office*